(12) United States Patent
Filipovic et al.

(10) Patent No.: US 11,786,146 B1
(45) Date of Patent: Oct. 17, 2023

(54) WIRELESS HUB SYSTEM AND METHOD

(71) Applicant: Micro Mobio Corporation, Palo Alto, CA (US)

(72) Inventors: Zlatko Aurelio Filipovic, San Jose, CA (US); Weiping Wang, Palo Alto, CA (US); Guan-Wu Wang, Palo Alto, CA (US); Adam James Wang, Palo Alto, CA (US); Brian Michael Wang, Palo Alto, CA (US)

(73) Assignee: Micro Mobio Corporation, Palo Alto, CA (US)

( * ) Notice: Subject to any disclaimer, the term of this patent is extended or adjusted under 35 U.S.C. 154(b) by 158 days.

(21) Appl. No.: 17/373,607

(22) Filed: Jul. 12, 2021

Related U.S. Application Data

(63) Continuation-in-part of application No. 16/595,914, filed on Oct. 8, 2019, now Pat. No. 11,058,326, which
(Continued)

(51) Int. Cl.
*H04W 4/90* (2018.01)
*A61B 5/11* (2006.01)
*G06F 1/16* (2006.01)
*A61B 5/332* (2021.01)
(Continued)

(52) U.S. Cl.
CPC .............. *A61B 5/1117* (2013.01); *A61B 3/14* (2013.01); *A61B 5/0022* (2013.01); *A61B 5/01* (2013.01); *A61B 5/02438* (2013.01); *A61B 5/1112* (2013.01); *A61B 5/332* (2021.01); *A61B 5/6831* (2013.01); *A61B 5/6898* (2013.01); *A61B 5/742* (2013.01); *A61B 5/748* (2013.01); *G06F 1/163* (2013.01); *G06F 1/1628* (2013.01); *G06F 1/1632* (2013.01); *G06F 1/1633* (2013.01); *G06F 1/1698* (2013.01); *G06F 1/183* (2013.01); *G06F 21/32* (2013.01); *G06F 21/70* (2013.01); *H02J 50/20* (2016.02); *H04B 1/385* (2013.01); *H04B 1/3888* (2013.01);
(Continued)

(58) Field of Classification Search
CPC .................. H04W 84/04; H04W 88/08; A61B 2560/0257; A61B 3/14; A61B 5/742; A61B 5/6898; A61B 5/002; A61B 5/02438; A61B 5/01; H04M 1/72412; H04M 1/72409; G06F 2200/1633; G06F 1/1698; G06F 1/1628; G06F 21/32; H02J 7/0044; H01Q 21/205; H04B 1/385
See application file for complete search history.

(56) References Cited

U.S. PATENT DOCUMENTS 5,960,074 A   9/1999   Clark
5,991,599 A   11/1999  Uchikawa
(Continued)

*Primary Examiner* — Congvan Tran
(74) *Attorney, Agent, or Firm* — ROARK IP

(57) ABSTRACT

A wireless hub includes a vehicle power connector that can draw power from a vehicle battery on a vehicle, a first wireless transmission circuit that can send or receive data with base stations in a long-range wireless network, a second wireless transmission circuit that can provide a short-range wireless network and to transfer data to and from electronic devices, and a network processor that can process data in the first wireless transmission circuit and the second wireless transmission circuit. The wireless hub has an antenna array for millimeter wave communications.

20 Claims, 28 Drawing Sheets

Related U.S. Application Data is a continuation-in-part of application No. 15/614,555, filed on Jun. 5, 2017, now Pat. No. 10,437,295, which is a continuation-in-part of application No. 14/803,828, filed on Jul. 20, 2015, now Pat. No. 9,671,835, which is a continuation of application No. 13/831,663, filed on Mar. 15, 2013, now Pat. No. 9,086,847.

(60) Provisional application No. 62/757,052, filed on Nov. 7, 2018, provisional application No. 61/705,383, filed on Sep. 25, 2012.

(51) Int. Cl.

| | | |
|---|---|---|
| *H04B 1/3888* | (2015.01) | |
| *H04M 1/02* | (2006.01) | |
| *G06F 1/18* | (2006.01) | |
| *G06F 21/32* | (2013.01) | |
| *G06F 21/70* | (2013.01) | |
| *A61B 3/14* | (2006.01) | |
| *A61B 5/01* | (2006.01) | |
| *A61B 5/00* | (2006.01) | |
| *A61B 5/024* | (2006.01) | |
| *H04B 1/3827* | (2015.01) | |
| *H02J 50/20* | (2016.01) | |
| *H04M 1/72409* | (2021.01) | |
| *H04M 1/18* | (2006.01) | |
| *H04M 1/72412* | (2021.01) | |
| *H04W 84/04* | (2009.01) | |
| *H04W 84/12* | (2009.01) | |
| *H04W 4/80* | (2018.01) | |
| *H04W 88/08* | (2009.01) | |

(52) U.S. Cl.
CPC ... *H04M 1/0254* (2013.01); *H04M 1/724098* (2022.02); *H04W 4/90* (2018.02); *A61B 2560/0242* (2013.01); *A61B 2560/0252* (2013.01); *A61B 2560/0257* (2013.01); *A61B 2562/0219* (2013.01); *H04M 1/185* (2013.01); *H04M 1/72412* (2021.01); *H04W 4/80* (2018.02); *H04W 84/04* (2013.01); *H04W 84/12* (2013.01); *H04W 88/08* (2013.01)

(56) References Cited

U.S. PATENT DOCUMENTS

| | | | |
|---|---|---|---|
| 6,154,658 | A | 11/2000 | Caci |
| 6,345,186 | B1 | 2/2002 | Schultz |
| 6,367,022 | B1 | 4/2002 | Gillespie |
| 6,442,018 | B1 | 8/2002 | Dinkin |
| 6,448,930 | B1 | 9/2002 | Judd |
| 6,601,176 | B1 | 7/2003 | Alexander |
| 6,778,895 | B1 | 8/2004 | Schwab |
| 6,792,296 | B1 | 9/2004 | Van Bosch |
| 6,816,731 | B1 | 11/2004 | Maruyama |
| 6,973,333 | B1 | 12/2005 | O'Neill |
| 7,047,339 | B2 | 5/2006 | Oakley |
| 7,057,591 | B1 | 6/2006 | Hautanen |
| 7,228,211 | B1 | 6/2007 | Lowrey |
| 7,265,970 | B2 | 9/2007 | Jordan |
| 7,324,840 | B2 | 1/2008 | Miyazaki |
| 7,558,057 | B1 | 7/2009 | Naksen |
| 7,742,739 | B2 | 6/2010 | Diaz Cervera |
| 7,743,999 | B1 | 6/2010 | Griffin |
| 8,035,577 | B2 | 10/2011 | Lafarre |
| 8,219,132 | B2 | 7/2012 | Hayashi |
| 8,274,446 | B2 | 9/2012 | Maxhimer |
| 8,319,742 | B2 | 11/2012 | Doktorova |
| 8,328,055 | B1 | 12/2012 | Snyder |
| 8,423,062 | B2 | 4/2013 | Yahagi |
| 8,605,421 | B2 | 12/2013 | Verschoor |
| 8,705,762 | B2 | 4/2014 | Davis |
| 8,896,992 | B2 | 11/2014 | Sherlock |
| 8,929,085 | B2 | 1/2015 | Franklin |
| 9,883,348 | B1 * | 1/2018 | Walker .............. H04W 4/029 |
| 2003/0115475 | A1 | 6/2003 | Russo |
| 2004/0021610 | A1 | 2/2004 | Hickel |
| 2004/0184466 | A1 | 9/2004 | Chang |
| 2004/0219876 | A1 | 11/2004 | Baker |
| 2005/0110640 | A1 | 5/2005 | Chung |
| 2005/0197771 | A1 | 9/2005 | Seick |
| 2005/0228297 | A1 * | 10/2005 | Banet ............... A61B 5/02116 |
| | | | 128/903 |
| 2006/0050475 | A1 | 3/2006 | Chen |
| 2006/0081624 | A1 | 4/2006 | Takada |
| 2006/0148533 | A1 | 7/2006 | Tanneberger |
| 2006/0181461 | A1 | 8/2006 | Leeper |
| 2007/0185627 | A1 | 8/2007 | Mavreas |
| 2008/0043692 | A1 | 2/2008 | Morita |
| 2008/0177436 | A1 | 7/2008 | Fortson |
| 2009/0131131 | A1 | 5/2009 | Wilson |
| 2009/0147758 | A1 | 6/2009 | Kumar |
| 2010/0128671 | A1 | 5/2010 | Chen |
| 2010/0218224 | A1 | 8/2010 | Gat |
| 2010/0240302 | A1 | 9/2010 | Buczkiewicz |
| 2010/0265144 | A1 | 10/2010 | Hoedl |
| 2010/0279602 | A1 | 11/2010 | Larsson |
| 2011/0022204 | A1 | 1/2011 | Hatfield |
| 2011/0136446 | A1 | 6/2011 | Komninakis |
| 2011/0143769 | A1 | 6/2011 | Jones |
| 2011/0153453 | A1 | 6/2011 | Ghafor |
| 2011/0169451 | A1 | 7/2011 | Stampfli |
| 2011/0222448 | A1 | 9/2011 | Ofek |
| 2011/0238855 | A1 | 9/2011 | Korunsky |
| 2011/0286428 | A1 | 11/2011 | Souissi |
| 2012/0027221 | A1 | 2/2012 | Davis |
| 2012/0039212 | A1 | 2/2012 | Kaliyaperumal |
| 2012/0088557 | A1 | 4/2012 | Liang |
| 2012/0162866 | A1 | 6/2012 | Bohn |
| 2012/0189410 | A1 | 7/2012 | Toebes |
| 2012/0212896 | A1 | 8/2012 | Schulz |
| 2012/0218695 | A1 | 8/2012 | Sakai |
| 2012/0241247 | A1 | 9/2012 | Choe |
| 2012/0247989 | A1 | 10/2012 | Cooper |
| 2012/0249064 | A1 | 10/2012 | Negishi |
| 2012/0249388 | A1 | 10/2012 | Hansen |
| 2012/0249887 | A1 | 10/2012 | Hr |
| 2012/0252411 | A1 | 10/2012 | Johnsgard |
| 2012/0257368 | A1 | 10/2012 | Bohn |
| 2012/0262345 | A1 | 10/2012 | Byun |
| 2012/0268891 | A1 | 10/2012 | Cencioni |
| 2012/0270600 | A1 | 10/2012 | Zelson |
| 2012/0281356 | A1 | 11/2012 | Brewer |
| 2012/0289338 | A1 | 11/2012 | Chen |
| 2012/0299966 | A1 | 11/2012 | Kim |
| 2013/0002543 | A1 | 1/2013 | Yau |
| 2013/0034234 | A1 | 2/2013 | Chen |
| 2013/0045683 | A1 * | 2/2013 | Wang .............. H04B 5/0037 |
| | | | 455/41.2 |
| 2013/0063873 | A1 | 3/2013 | Wodrich |
| 2013/0076614 | A1 | 3/2013 | Ive |
| 2013/0077228 | A1 | 3/2013 | Batio |
| 2013/0141299 | A1 | 6/2013 | Mast |
| 2013/0147330 | A1 | 6/2013 | DiFonzo |
| 2013/0288600 | A1 | 10/2013 | Kuusilinna |
| 2014/0012528 | A1 | 1/2014 | Carmel-Veilleux |
| 2014/0086586 | A1 | 3/2014 | Voutilainen |
| 2014/0159867 | A1 | 6/2014 | Sartee |
| 2014/0334098 | A1 | 11/2014 | Lauder |
| 2015/0301168 | A1 | 10/2015 | Brown |
| 2015/0303587 | A1 | 10/2015 | Pan |
| 2016/0379021 | A1 | 12/2016 | Bellows |
| 2019/0025857 | A1 | 1/2019 | Luckevich |
| 2019/0036209 | A1 | 1/2019 | Au |
| 2020/0229245 | A1 | 7/2020 | Wu |
| 2020/0235611 | A1 * | 7/2020 | Zeine ............... H02J 50/23 |
| 2022/0385325 | A1 * | 12/2022 | Guzik ............... H04W 4/38 |

* cited by examiner

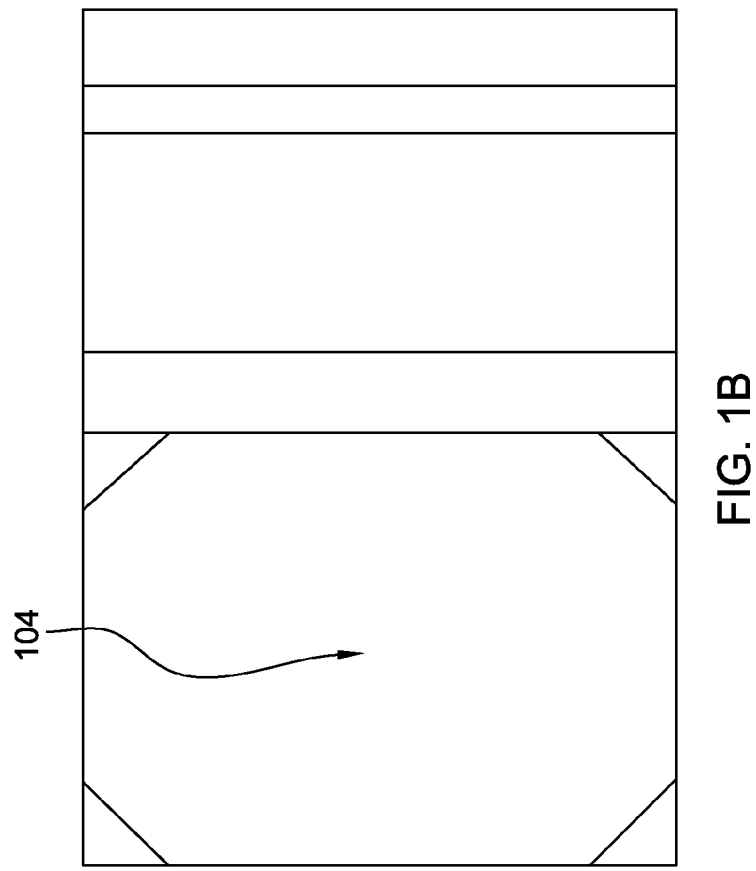
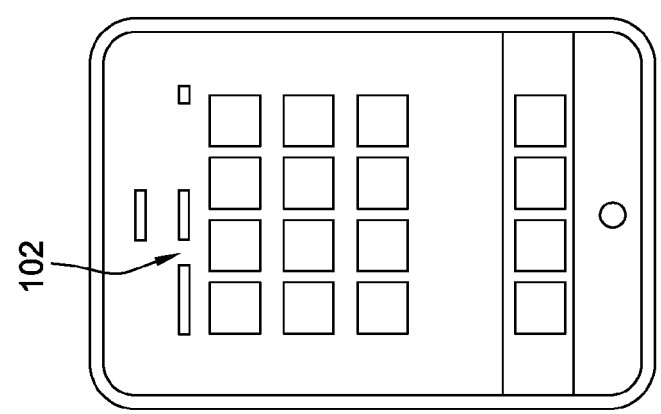

WIRELESS HUB SYSTEM AND METHOD

PRIORITY CLAIM

This patent application claims priority as a Continuation-In-Part of U.S. Patent application Ser. No. 16/595,914, filed on Oct. 8, 2019; which claimed priority to U.S. Provisional Patent Application 62/757,052, filed on Nov. 7, 2018 and as a Continuation-In-Part of U.S. patent application Ser. No. 15/614,555, filed on Jun. 5, 2017; which claimed priority as a Continuation-In-Part of U.S. patent application Ser. No. 14/803,828, filed on Jul. 20, 2015; which claimed priority as a Continuation of U.S. patent application Ser. No. 13/831,663, filed on Mar. 15, 2013; which claimed the benefit of U.S. Provisional Patent Application Ser. No. 61/705,383, filed Sep. 25, 2012; the aforementioned applications all being incorporated herein by reference in their entireties.

FIELD OF THE DISCLOSURE

The present disclosure relates generally to portable electronic devices and antenna arrays and, in particular, the present disclosure relates to a plurality of antenna arrays mounted on a platform on a vehicle.

BACKGROUND

There are presently a wide variety of portable electronic devices 102 as disclosed in FIG. 1A. The portable electronic devices may include cellphones such as the iPhone®, Nexus, Lumia and the like and tablet personal computers (PCs) such as the iPad®, Kindle® and similar type devices. These portable electronic devices are often protected by a simple case cover 104 as disclosed in FIG. 1B. These prior art case covers 104 typically do not contain any functional components beyond the protective cover itself.

SUMMARY

Aspects of the disclosure include a wireless hub comprising: a first wireless transmission circuit connected to a first antenna and configured to directly send or receive data in frequencies ranging from approximately 10 GigaHertz (GHz) to approximately 80 GHz; wherein the first antenna has a plurality of antenna flat panels each having antenna array elements which are capable of wirelessly sending and receiving millimeter wave signals to and from at least one base station and at least one wireless hub, wherein the plurality of antenna flat panels are arranged to provide surrounding coverage for transmission and reception of the millimeter wave signals; and a second wireless transmission circuit connected to a second integrated antenna and configured to provide a short-range wireless network capable of sending or receiving data to and from electronic devices in the short-range wireless network.

Aspects of the disclosure further include a wireless hub package comprising: a first wireless transmission circuit connected to a first antenna and configured to directly send or receive data in frequencies ranging from approximately 10 GigaHertz (GHz) to approximately 80 GHz with a base station and a plurality of vehicle wireless hubs; wherein the first antenna has a plurality of antenna flat panels each having antenna array elements which are capable of wirelessly sending and receiving millimeter wave signals to and from at least one base station and at least one wireless hub, wherein the plurality of antenna flat panels are arranged to provide surrounding coverage for transmission and reception of the millimeter wave signals; and a second wireless transmission circuit connected to a second package integrated antenna and configured to provide a short-range wireless network capable of sending or receiving data to and from electronic devices in the short-range wireless network.

Aspects of the disclosure further include a wireless hub package, comprising: a first wireless transmission circuit connected to a first antenna and configured to directly send or receive data in frequencies ranging from approximately 400 MegaHertz (MHz) to approximately 7 GigaHertz with base stations in a long-range wireless network and with another wireless hub; wherein the first antenna has a plurality of antenna flat panels each having antenna array elements which are capable of wirelessly sending and receiving millimeter wave signals to and from at least one base station and at least one wireless hub, wherein the plurality of antenna flat panels are arranged to provide surrounding coverage for transmission and reception of the millimeter wave signals; and a second wireless transmission circuit connected to a second integrated antenna and configured to provide a short-range wireless network capable of sending or receiving data to and from electronic devices in the short-range wireless network.

BRIEF DESCRIPTION OF THE DRAWINGS

FIG. 1A is a front view of a prior art mobile computing device.

FIG. 1B is a front view of a prior art simple case cover for a mobile computing device.

DETAILED DESCRIPTION

Although particular aspects or features of the following disclosure may be described with reference to one or more particular embodiments and/or drawings, it should be understood that such features are not limited to usage in the one or more particular embodiments or drawings with reference to which they are described, unless expressly specified otherwise. The functionality and/or the features of the embodiments that are described may be alternatively embodied by one or more other devices which are described but are not explicitly described as having such functionality/features.

Current mobile computing device covers are limited in their functionality by mainly providing protection from environmental shocks for mobile computing devices. However, the personal cloud cover case (or "PCCC") as disclosed in this application by providing electronic component accessories and functionalities to the cover case enhances the ability of a mobile computing device located inside the PCCC to provide cloud computing services. Cloud computing is the use of computing resources that are delivered as a service over a network (such as the Internet) and which reside in the "cloud". The mobile computing device in the case could be an iPad®, iPhone®, PC tablet, Android® based tablet, TouchPad, Nexus 7®, Slate® or the like.

Figure 2A:
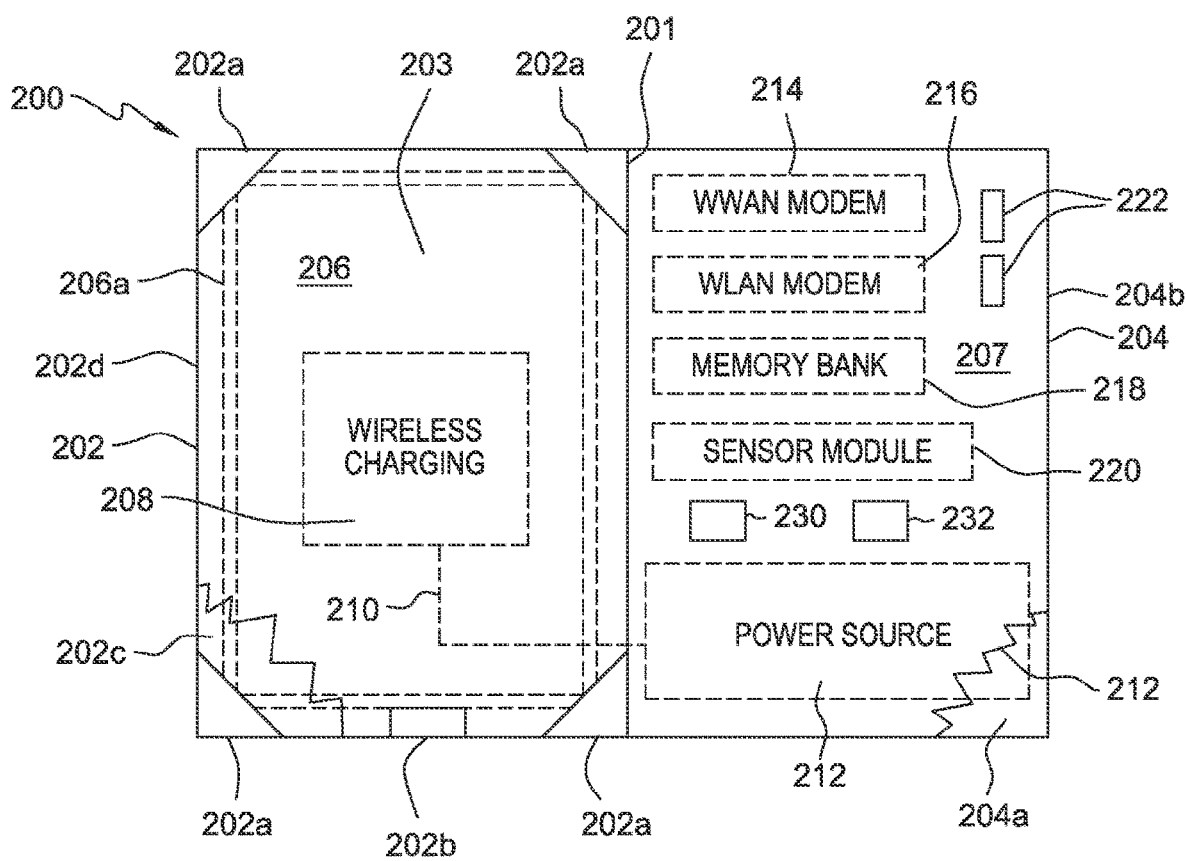
FIG. 2A is a front view of a personal cloud case cover (PCCC).

FIG. 2A is a front view of a PCCC 200 which is shown in an open position. The case 200 provides a personal cloud to the user and access to a wireless network (such as 3G, 4G, 5G, WiFi, SuperWifi, and similar technologies) of a mobile computing device (not shown) stored in the case 200. The case 200 may be made of any material (hard and/or soft) that makes the case lightweight but durable and resilient such as plastic, silicone, ceramic, fabric, leather, steel, aluminum, fiberglass, titanium, Kevlar, or rubber. The case 200 could be a continuous piece of material with a flexible (or bendable) area 201 located between two opposing panels (first panel 202 and second panel 204) which pivot together around a compartment 203 for containing the mobile computing device. In an alternative embodiment, the case 200 could be made up of plurality of attached sections (201, 202 and 204). First panel 202 also has 4 sleeves 202a to hold the mobile computing device in place in the case 200. In alternative embodiments, the mobile computing device could be attached to the PCCC 200 using a plurality of magnets (instead of the sleeves 202a) positioned under the mobile device, rubber straps or other similar attachment methods.

The first panel 202 is constructed in layers and includes inner first panel layer 202c, outer first panel layer 202d and embedded circuit board 206. Typically, from the front view the circuit board 206 cannot be seen since it is located underneath the first panel layer 202c shown in cutaway but which is designed to cover substantially the entire first panel 202. An antenna 206a is located on the circuit board 206 and may be in contact with the mobile communication device wirelessly, through physical contact or by connector 202b. Connector 202b is optional and in alternative embodiments it would not be present. The antenna 206a will allow for better transmission and reception on the part of the mobile communication device. The antenna 206a can be a "chip" antenna, printed circuit board (PCB) antenna or the like covering a plurality of wireless bands (e.g., 400 MHz-3.6 GHz). Alternatively, a PCB antenna may be used, and the antenna 206a will be printed directly onto the circuit board 206. Also located on the board 206 is a two-way wireless charging unit 208 which is in substantial proximity to the resting place of the mobile communication device in the cover 200. The charging unit 208 is designed such that when the mobile communication device is in proximity to the charging unit an electromagnetic field generated by the charging unit pulls the communication device into proper position and alignment for optimal charging (i.e., charging coil alignment). The wireless charging unit 208 is connected through a bidirectional electrical link 210 to power source 212 located on a circuit board 207 embedded in the second panel 204. The bidirectional electrical link 210 is an example of the plurality of electrical connections that are made throughout the case 200 but which are not necessarily shown in the Figures. Link 210 might be in the form of a ribbon cable so as not to be damaged with the opening and closing of the case 200. The wireless charging unit 208 is capable of wirelessly charging the mobile communication device with power received from the power source 212 or wirelessly receive power from the mobile communication device and transfer it to the power source 212. The wireless charging unit 208 may operate by magnetic resonance, inductive charging, or power over radio frequency (RF) or similar wireless charging methods. The power source 212 is used to power the plurality of components located throughout the cover 200 and, as described, can also be used as a backup battery for the mobile computing device when the voltage in the battery of the mobile computing device falls below a predetermined level.

The second panel 204 can be made up of an inner second panel 204a and an outer second panel 204b containing the embedded circuit board 207 but which typically cannot be seen from a front view since it is covered by inner second panel layer 204a. The inner second panel layer 204a covers substantially the entire second panel 204 but is only partially shown in cutaway so as to illustrate the components mounted on the circuit board 207 in the outer second panel 204b. It should be understood that the inner second panel layer 204a and the outer second panel layer 204b can be coupled together by a variety of methods such as ultrasonic bonding, mechanical fasteners, adhesives, or solvents. In alternative embodiments, the inner second panel 204a may be entirely or substantially detachable from the outer second panel 204b; the inner second panel 204a may be a closure flap that is fastened close by means of adhesive, a snap button, or Velcro or the inner second panel 204a may not be present at all so as to allow easy access to the components mounted on the board 207 in the outer second panel 204b. The case 200 may further be made up of a plurality of modules 214, 216, 218 and 220 mounted on the circuit board 207 which allow the PCCC 200 to have multi-functional capability. The modules may be made of low profile components which help minimize the thickness of the cover. The plurality of modules may be permanently mounted, may snap-in to the board 207 or may be some combination thereof. First module 214 may include a wireless wide area network modem (WWAN). The WWAN could include baseband, a radio frequency integrated circuit (RFIC), a radio frequency front-end module (RF FEM), Envelope Tracking (ET), Power Management IC (PMIC), and other connected components to link the mobile computing device to a mobile network such as a 3G, 4G or future generation network. Second module 216 may include a wireless local area network (WLAN) modem for a mobile computing device to connect to a local router and then to 2G, 3G and 4G networks. The WLAN modem can be baseband, RFIC, RF FEM and other connectivity components. The case 200 may contain near field communications (NFC) technology which may be used for contactless short range communications based on RF identification standards (RFID) using magnetic field induction to enable communication between the electronic components in the case 200 over short distances such as a few centimeters. In other embodiments, the WLAN modem connection could be made using wireless protocols such as WiFi, SuperWiFi (i.e., the next generation WiFi with superior range), Bluetooth, wireless for high definition multimedia interface (WHDMI), or the like. Third module 218 may be internal storage such as solid-state drives (SSD) or flash memory (e.g., MultiMedia Card (MMC), electronic MMC (eMMC) or the like). Fourth module 220 may contain a sensor chip that is able to detect biometrics inputs such as finger prints, eye movement, face shape, and the like. Module 220 can be used for functions such as a security feature for allowing or denying access to the electronic components in the case, gaming, and medical purposes (e.g., measuring blood cell count and the like). The second panel 204 may also include a smart feature such as a synchronization input 230 (e.g., such as a button, touch screen, or the like) that allows the plurality of electronic components (e.g., module 218) in the PCCC 200 to be synched to other networked devices in the cloud when operated. This input 230 would primarily be used when a mobile communication device is not present in the PCCC 200. The input 230 may be used to backup data stored in the components of the PCCC 200. Reference 232 in FIG. 2A shows a controller which may be used with the mobile communication device or in the absence of the mobile device to control the electronic components in the PCCC 200. For example, in the synching process when input 230 is operated the controller 232 would direct the synching operation.

Figure 2B:
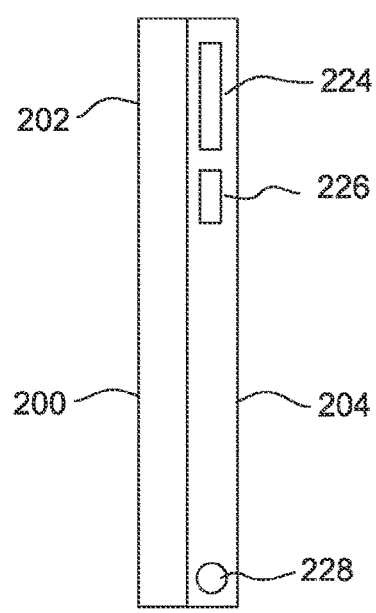
FIG. 2B is a side view of the PCCC of FIG. 2A.

FIG. 2B is a side view of the case 200 in a closed position. Data connection ports 224 and 226 provide communication capabilities to the case 200.

Ports 224 and 226 may be a mini universal serial bus (USB), micro universal USB port or an audio visual (AV) connector such as a high definition multimedia interface (HDMI) port and the like. Charging port 228 can be connected to the grid or other power source to feed the power source 212.

Figure 3:
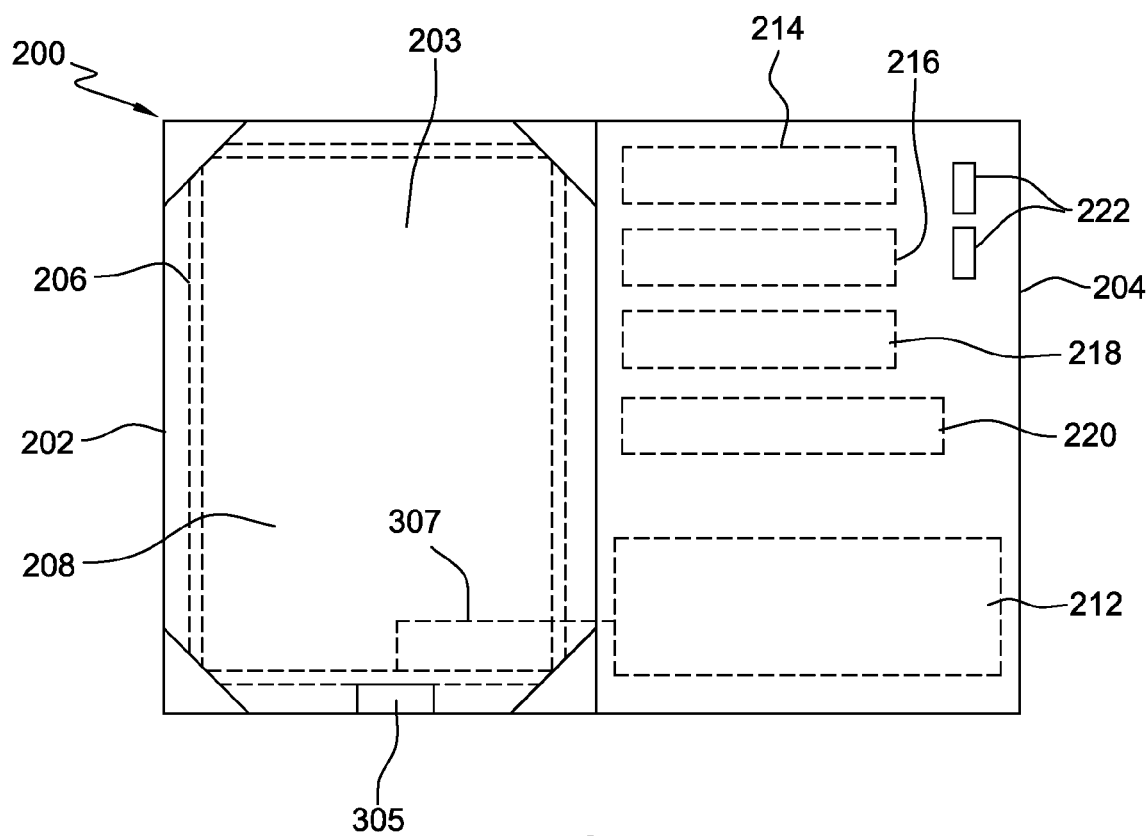
FIG. 3 is a front view of a second embodiment of the PCCC.

FIG. 3 is a second embodiment of the PCCC 200. Common numbering is used in FIGS. 3 though 9 and FIGS. 2A to 2B to denote similar elements. In this second embodiment, instead of wireless charging, a docking bay 305 having a set of electrical contacts is configured to electrically engage with the input/output contacts on a mobile communication device. The docking bay 305 may be a standard connector that allows the mobile communication device to receive power through line 307 from power source 217.

Figure 4:
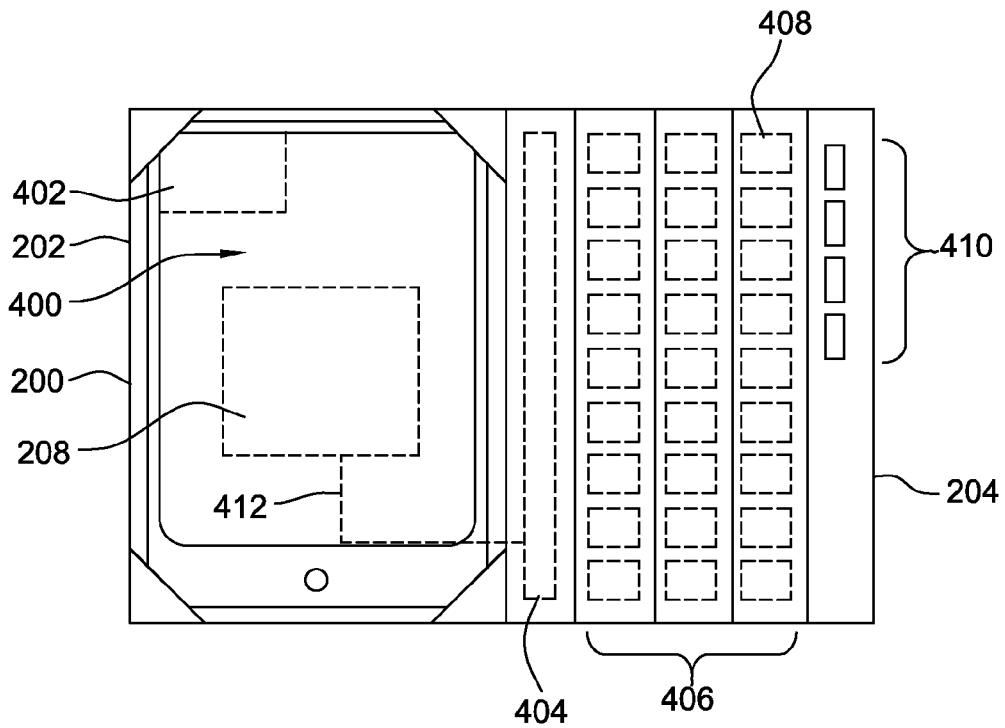
FIG. 4 is a front view of a third embodiment of the PCCC.

FIG. 4 illustrates a third embodiment of the PCCC 200. A mobile communication device 400 can be connected to a local area or wide area network through wireless modem 402 which may be 3G, 4G, 3G/4G, 5G, WHDMI, Bluetooth, WiFi, SuperWiFi, and other wireless standard. Module 404 is a replaceable, rechargeable battery that is charged through line 412 from the wireless charger 208 and receives power from mobile communication device 400. Module 404 performs the same function as power source 212 in FIG. 2 but is arranged differently in the case 200 as shown in FIG. 4. The wireless charger 208 may be located on the first panel 202 beneath the mobile communications device 400. The module 404 can also be charged from a power outlet when the case 200 is plugged in. The module 404 can be used as a power source for other modules (reference numerals 408 and 410 as discussed below) located in the case 200. An embedded memory bank 406 includes a plurality of memory modules and is mounted on the second panel 204. The memory bank modules may be 12020 MegaByte (MB), 1 Gigabyte (GB), 1 Terabyte (TB) or the like in memory size. Memory slots 410 are capable of holding additional memory such as removable micro-Secure Digital (micro-SD) memory cards for storage expansion.

Figure 5:
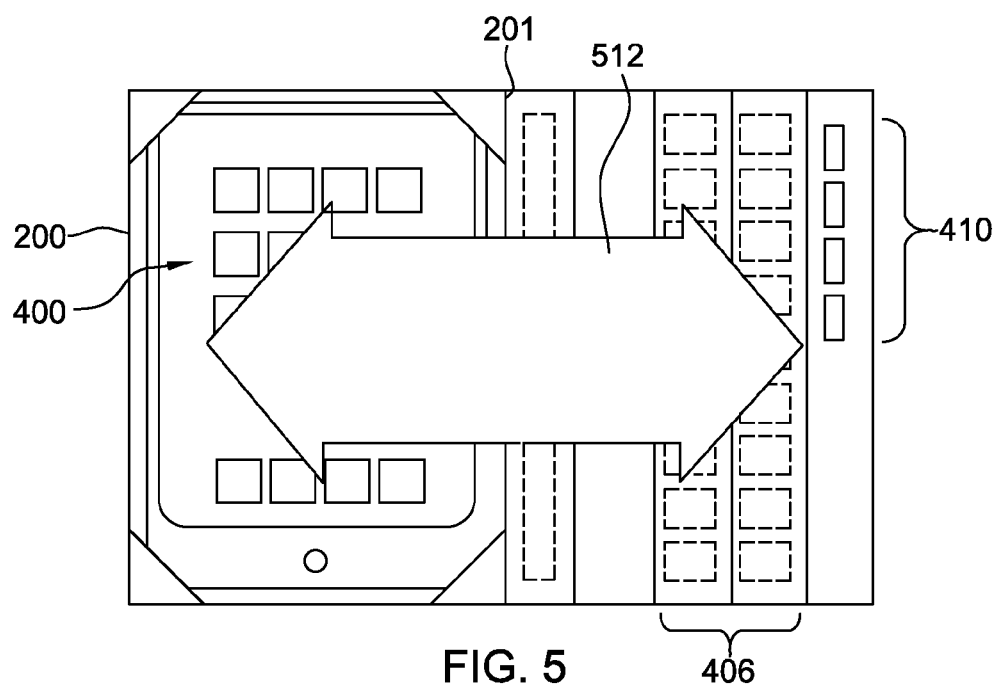
FIG. 5 is a front view of a fourth embodiment of the PCCC.

FIG. 5 illustrates a fourth embodiment of the PCCC 200 which demonstrates that the plurality of modules are detachable and could be two instead of three in the case 200. Also, FIG. 5 discloses a wireless data connection 512 between the device 400 and memory bank 406 using WiFi, SuperWiFi or Bluetooth protocols. In alternate embodiments, the data connection 512 could be a hardwired such as a Universal Serial Bus (USB), microUSB, miniUSB, or HDMI (with the data line being flexibly bendable across the flexible region 201 in the form of a ribbon cable or the like). In other embodiments, the connection could also be an optical wireless link or cable such as infrared. The data transfer could be bi-directional to allow for read and write both ways from device 400 to memory 406 and from memory 406 to device 400.

Figure 6A:
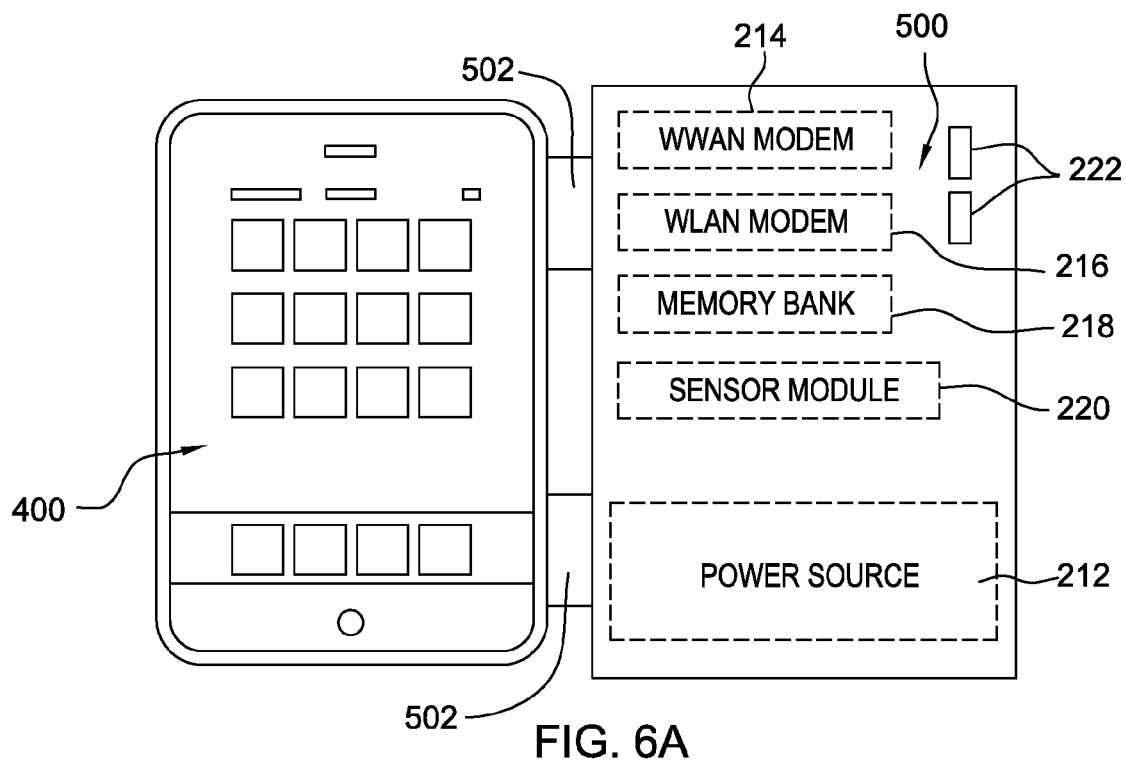
FIG. 6A is a front view of a fifth embodiment of the PCCC.
Figure 6B:
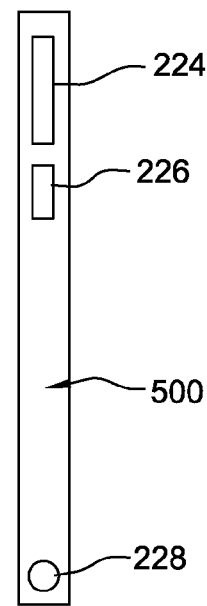
FIG. 6B is a side view of the PCCC of FIG. 6A.

FIG. 6A is another embodiment of the PCCC with just one panel 12020 attached to the device 400 through attachments 12022. Attachments 12022 may be magnets, clip ins, connectors or some other type of hinge. The attachments 12022 may internally include a plurality of electrical links to provide power from the power source 212 to the mobile communication device 400 as well as provide data communications between the modules on the panel 12020 and the device 400. The power source 212 may include a wireless charging unit so as to wirelessly charge the device 400. The charging may take place when the panel 12020 is in a lateral position relative to the device 400 as shown in FIG. 6A. In an alternative embodiment, the panel 12020 may be folded over and placed in contact with the device 12020 to establish an electrical power link between the power source 212 and electrical contacts located on the device 400. Also, similar to the embodiment of FIG. 5, a wireless data connection may be established between the device 400 and the plurality of modules on the panel 12020 (items 214, 216, 218, 220, and 222). FIG. 6B is a side view of the panel 12020 showing the connection ports 224, 226, and 228 which serve the same functions as described in connection with FIG. 2B above.

Figure 7:
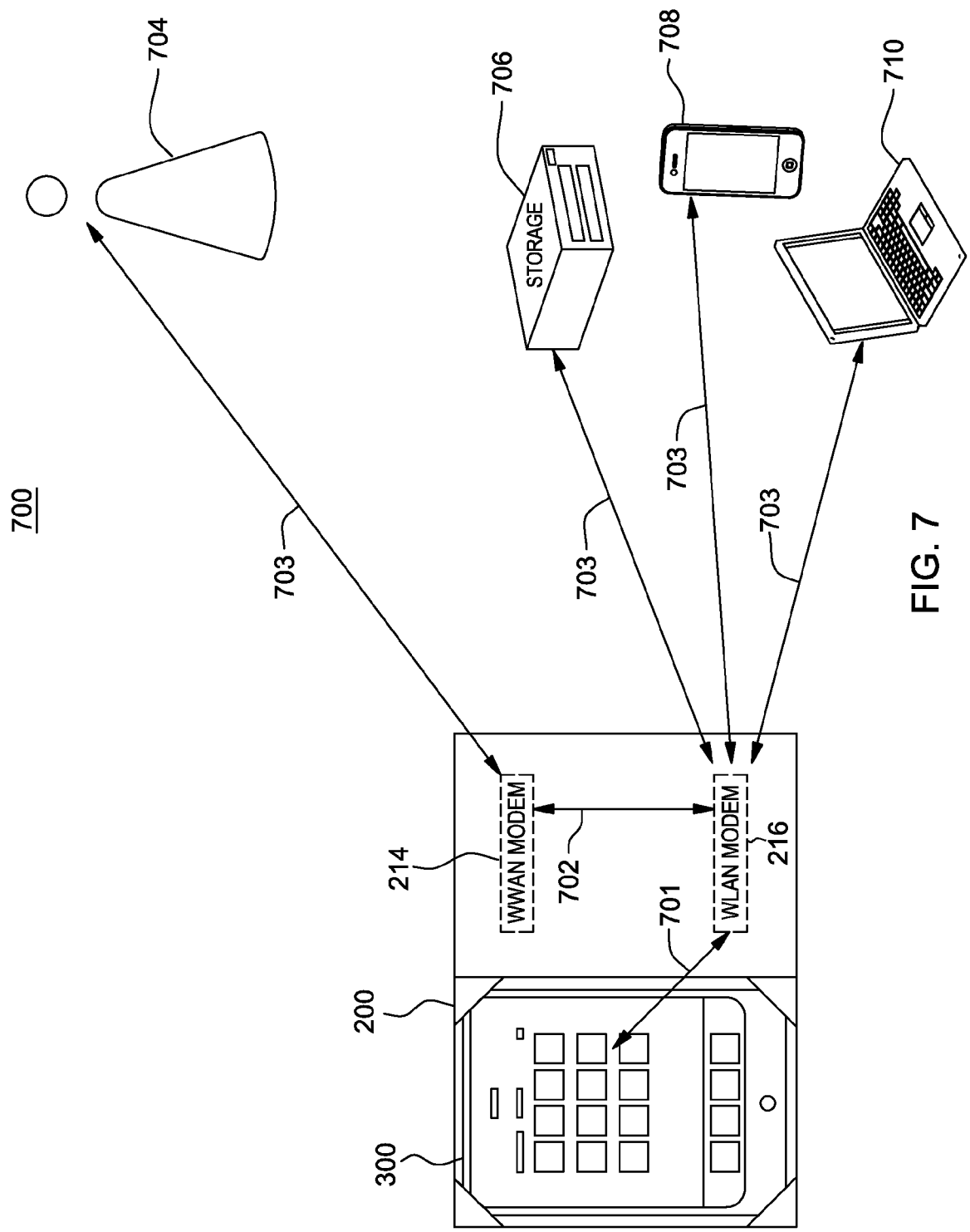
FIG. 7 is a schematic diagram of a PCCC in a cloud/networked environment utilizing 3rd Generation (3G), 4th Generation (4G), Fifth Generation (5G) and similar wireless connections.

FIG. 7 illustrates the mobile communication device 300 and PCCC 200 operating in a cloud (or networked) environment 700. Storage 706, mobile phone 708 and personal computer (PC) 710 are part of the cloud upon which the mobile communications device 300 and PCCC 200 can exchange data and synchronize through a plurality of wireless links 703. The WWAN modem module 214 and WLAN modem module 216 of FIG. 7 operate in a similar manner as described in connection with FIG. 2A above. The mobile computing device 300 communicates through a bi-directional wireless link 701 with the WLAN modem 216 using Bluetooth, WiFi, SuperWiFi and similar wireless standards. In another embodiment, the link 701 may be a wired link. WLAN modem 216 then can read and write wirelessly in a local environment with storage 706. The WLAN modem 216 can also communicate with another mobile phone 708 and PC 710. Alternatively, the mobile computing device 300 can communicate through WLAN 216 over a bi-directional link 702 with WWAN modem 214. WWAN modem 214 can communicate wirelessly using 3G/4G protocols over longer distances than the WLAN modem 216 with a cell tower 704 and then to the Internet. In the environment of FIG. 7, the case 200 is acting as "hotspot". As a hotspot, the case 200 offers network (e.g., Internet) access over the WWAN modem 214 or WLAN modem 216.

Figure 8:
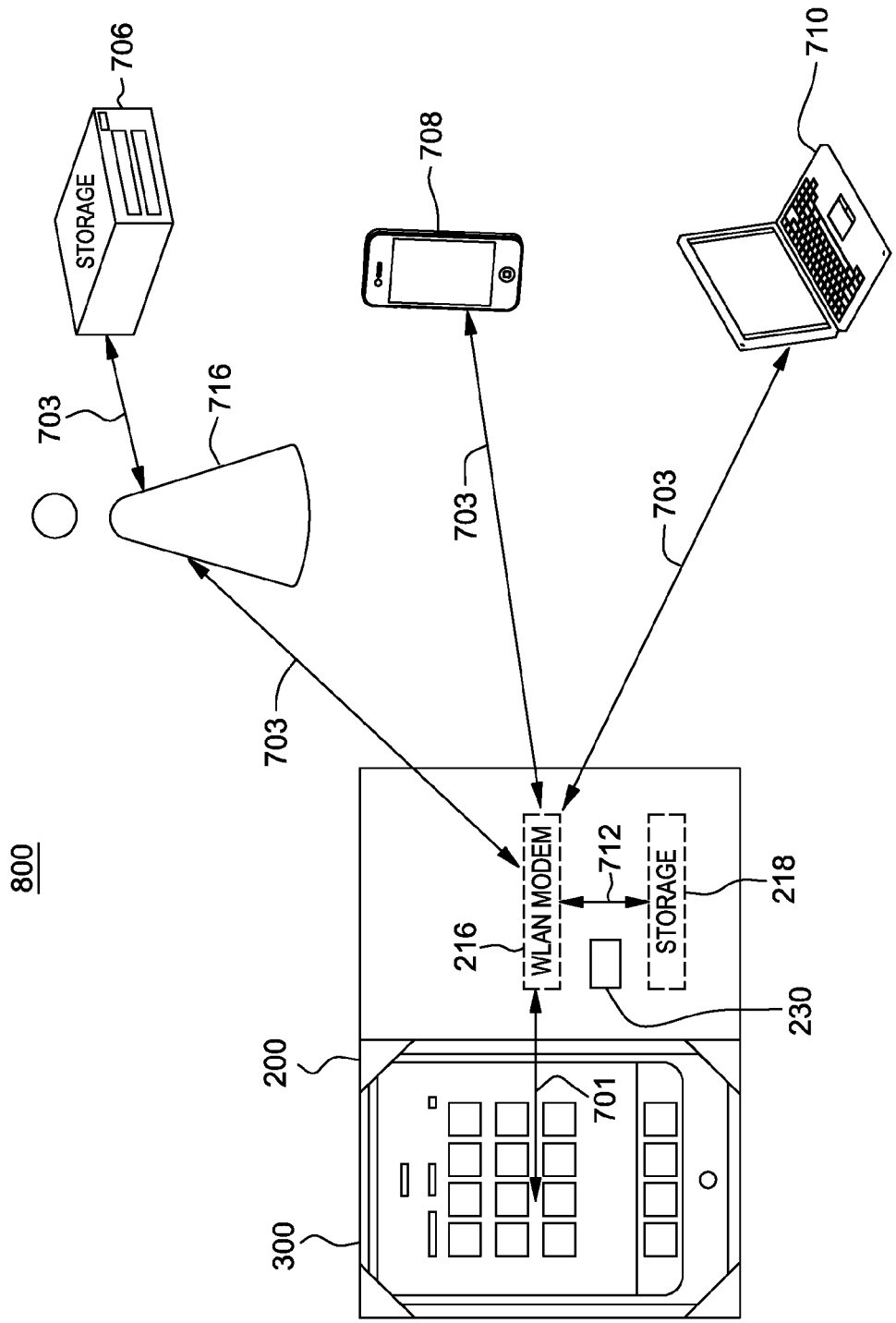
FIG. 8 is a schematic diagram of the PCCC in another cloud/networked environment system.

FIG. 8 illustrates another variation of the mobile communication device 300 and the case 200 in operation 800. This arrangement allows the local storage 218 to have access to a plurality of devices in the cloud such as the communication device 708, PC 710 and storage 706 through local wireless router (or access point) 716. As previously discussed in connection with FIG. 2A, sync input 230 can be operated when the mobile communication device is not present in the case 200 to backup all data contained in the components in the case 200 to the cloud (e.g., devices such as 706, 708, 710 and other devices). Another advantage is that this system allows for the formation of a "pass through Internet" from the mobile communication device 300 to devices 706, 708, 710 and a network (e.g., the Internet). WLAN modem 216 is connected to memory storage 218 through link 712 and is capable of establishing wireless communications with both the mobile communication device 300 and the devices 706, 708, and 710. In operation, the mobile communication device 300 establishes a wireless connection 701 through WiFi, SuperWiFi, 4G or the like to the WLAN modem 216. Through WLAN modem 216, the communication device 300 is capable of connecting to the memory storage 218 (e.g., providing information or instructions regarding reading and/or writing) while simultaneously browsing the Internet through wireless link 703 to access point 716. The term simultaneously as used herein shall mean immediate or nearly immediate succession in time. In another embodiment, the connection from the mobile communication device to the memory storage 218 could be wired. Alternatively, the communication device could be simultaneously connecting to memory storage 218 while communicating with devices 706, 708 and 710 through wireless links 703. This pass through Internet feature allows the user to access data stored in the memory 218 and browse the Internet simultaneously from a single device (mobile communication device 300) or a plurality of devices. The WLAN modem 216 is designed to operate in one or more bands and cover one or more wireless standards. The bands may include first and second frequency bands (e.g., 2 GHz and 5 GHz). The WLAN modem 216 may use the first band for the transmission of information from memory storage 218 to the mobile communication device 300 and the second band for communications with the access point 716 (and thereby the Internet).

Figure 9:
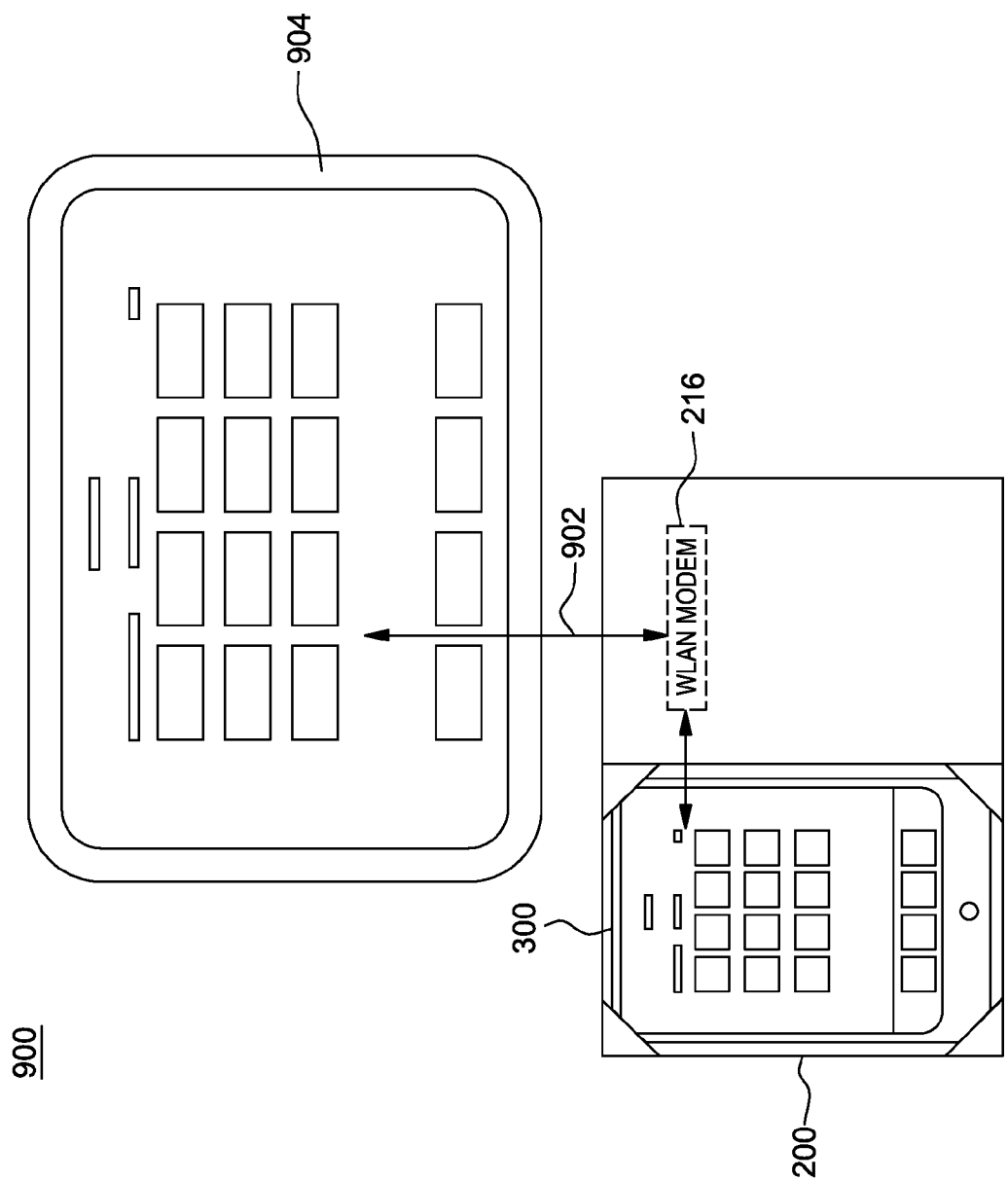
FIG. 9 is a view of the PCCC operating with a large external monitor.

FIG. 9 illustrates another environment 900 in which the PCCC 200 may operate. The PCCC 200 allows the mobile communication device 300 to link through WLAN 216 and wireless link 902 with large external monitor 904 using WiFi, SuperWiFi, WHDMI, or the like and display information (e.g., video, audio, or text) from either the mobile communication device 300, the memory storage or another source (e.g., devices 706, 708, 710) on to the monitor 904.

FIGS. 10-13B illustrate another environment 1000 in which the PCCC 200 may operate. As new wireless and fixed standards (such as 4G, 5G, 802.11ad, and the like) keep pushing the operating frequencies into millimeter (mm) wave spectrum (e.g., 28 GHz, 40 GHz, 60 GHz, 70 GHz, 100 GHz) it becomes harder and harder (due to higher penetration loss and path loss) to get the signal inside buildings, houses, cars, and even mobile phones (as phone casings might prevent millimeter wave signals from getting in or out). These challenges limit the usability of mm waves and make mm systems very expensive to deploy. The disclosed embodiments described herein help to make mm wave signal penetration possible.

In FIGS. 10-13B, PCCC 200 is an alternative embodiment in which an antenna array 240 is mounted in the case. (In alternative embodiments of FIGS. 10-13B it could be the one panel version of PCCC 12020 shown in FIGS. 6A-6B used instead of the multiple panel version of the PCCC 200 but FIGS. 10-13B will use PCCC 200 for description purposes). PCCC 200 can be any of the embodiments disclosed in FIGS. 1-9 which either further include antenna array 240 or where antenna array replaces elements and or modules of the PCCC 200 (or PCCC 12020) disclosed in FIGS. 1-9. Antenna 240 can be a low cost antenna array 240 made up of cells in an N×N array (e.g. 2×2, 2×2, 4×4, 8×8, or the like) or an M×N array (e.g., 1×4, 2×4, 2×5, 2×8, or the like). The antenna array 240 could be made on circuit boards 206 or 207, it could be a chip antenna on the circuit boards 206 or 207, or it could be a multilayer antenna on the circuit boards 206 or 207. The antenna array 240 can be used to increase the gain of the signal 1004, can be used for beam forming and beam steering, phase shifting, and/or gesture tracking. The antenna array 240 may be in contact with the mobile communication device (not shown) wirelessly, through physical contact or through a connector (e.g., 202b) or an electrical link (or links) running through circuit boards 206 and 207. In alternative embodiments, the antenna array 240 could be attached to the side or back of the mobile communication device (such as when it is the form of embodiment PCCC 12020) as well. The antenna array 240 may also be coupled to and controlled by the other elements and modules in the PCCC 200 (or PCCC 12020) through electrical links in the circuit boards 206 and/or 207 and implemented using hardware, software, firmware, middleware, microcode, or any combination thereof.

Antenna array 240 may be configured in a plurality of ways. Antenna 240 may be made up of cells in an N×N or M×N array configuration as discussed above. The array 240 may made of a low-cost material and a number of different substrates could be used each having their own fabrication tolerances and electrical and mechanical properties. The array 240 can be made of an Anion CLTE-XT (PTFE ceramic), a Rogers RT 5880/RO 3003 (PTFE glass fiber), a Rogers Liquid Crystal Polymer (LCP), a low temperature cofired ceramic (LTCC), a Parylene N dielectric, a polytetrafluoroethylene (PTFE) ceramic, a PTFE glass fiber material, a silicon material, a Gallium Arsenite (GaAs) material, an Alumina material, a Teflon material, a Duroid material or any other material that can produce thin (about 2-4 mils in thickness) metallized layers. In one embodiment, the layers may be stacked to form a multi-layer array architecture. With the antenna array 240 printed on a thin film material, mm wave signals can penetrate through any object efficiently and at low cost. The PCCC 200 surrounding array 240 may also be made of glass, plastic, etc.

Figure 10:
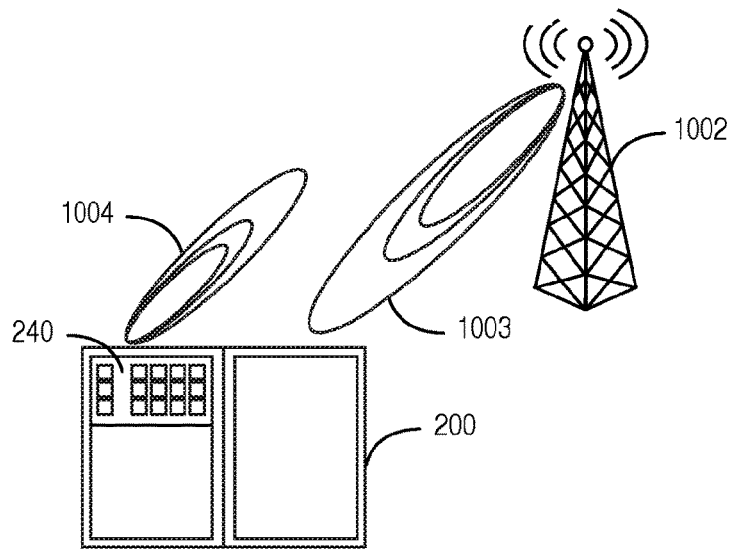
FIG. 10 is a PCCC 200 with an antenna array 240 in communication with a communication tower (e.g., cell tower, base station or the like) 1002 using millimeter (mm) wave signals 1003, 1004.

In FIG. 10, in operating environment 1000 antenna array 240 allows PCCC 200 to communicate with a communication tower (e.g., cell tower, base station or the like) 1002. Communication tower 1002 and antenna array 240 could communicate with each other using, for example, time domain (TDD) or frequency domain signals (FDD) 1002, 1003 (and 1302 as discussed below). Downlink signal (or beam) 1003 coming from communication tower 1002 and uplink signal (or beam) 1004 coming from array 240 are formed and steered to allow mm wave signal communications between the array 240 and communication tower 1002. The antenna array 240 may be located by communication tower 1002 using Global Positioning Satellite (GPS) technology or by 3G/4G/5G technology. Beams 1003 and 1004 (and 1302) may operate in the range of approximately 3 GigaHertz (GHz) to approximately 100 GHz or even higher. Typically, beams 1003 and 1004 (and 1302) will operate approximately in a range of plus or minus(+/−) 12% of mm wave frequency signals such as 24 GHz, 28 GHz, 39 GHz, 60 GHz, and/or 77 GHz (e.g., for 24 GHz the signal would range from approximately 21.12 GHz to approximately 26.88 GHz). Alternatively, mm wave beams 1003 and 1004 (and 1302) can operate in the following ranges: approximately 3.3 GHz to approximately 3.4 GHz; approximately 3.4 GHz to approximately 3.6 GHz; approximately 3.6 GHz to approximately 3.8 GHz; approximately 5.11202 GHz to approximately 5.925 GHz; approximately 24.25 GHz to approximately 27.5 GHz; approximately 31.8 GHz to approximately 33.4 GHz; approximately 37.0 GHz to approximately 40.5 GHz; approximately 40.5 GHz to approximately 42.5 GHz; approximately 42.5 GHz to approximately 43.5 GHz; approximately 45.5 GHz to approximately 47 GHz; approximately 47.0 GHz to approximately 47.2 GHz; approximately 47.2 GHz to approximately 1202.2 GHz; and approximately 1202.4 GHz to approximately 52.8 GHz.

Figure 11:
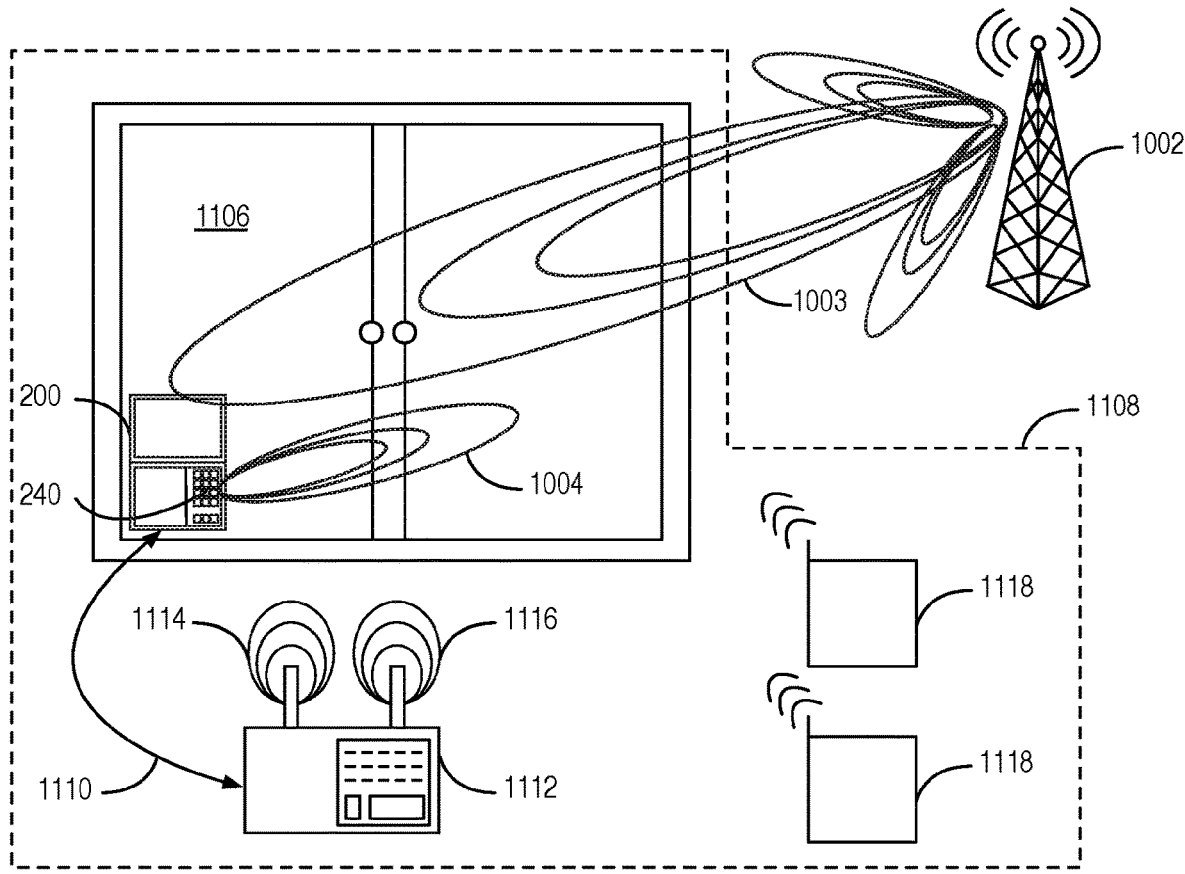
FIG. 11 illustrates an environment in which a communication tower 1002 communicates through downlink signal 1003 and uplink signal 1004 back and forth in mm wave signals between a PCCC 200 with an antenna array 240 mounted on a window 1106 inside a building 1108.

FIG. 11 shows an alternative operating environment 1100 in which a communication tower 1002 communicates through downlink signals (or beams) 1003 and 1004 back and forth in mm wave signals with a PCCC 200 (or PCCC 12020) with an antenna array 240 mounted on a window 1106 inside a building 1108 (or outside the building, e.g., resting on a ledge). PCCC 200 may be mounted to window 1106 through adhesives such as suction cups or through some other type of mounting mechanisms. The mm waves 1003 sent from communication tower 1002 can be received at PCCC 200. PCCC 200 could then down convert the mm wave signals 1003 using other modules in the case 200 to lower frequency signals (e.g., approximately 2 GHz, 5 GHz, 8 GHz or the like). In some embodiments, these lower frequency signals are forwarded from a connection on the case 200 (e.g., 202b) through a wired coupling (e.g., a cable) 1110 to user equipment device (or a plurality of user equipment devices) 1112. PCCC 200 can also send signals wirelessly to user equipment device 1112 (e.g., using 802.11ad and/or 802.11ax). User equipment device (UED) 1112 located in the building 1108 has the ability to forward the signal through UED signals 1114 and 1116 (which typically are at different frequencies such as WiFi, Bluetooth, Zigbee, etc.) to a plurality of devices 1118 such as phones, tablets, and/or televisions. Wired coupling 1110 not only carries the RF signals received and sent to and from the antenna array 240 but it may also provide control signals and power supply for the antenna array 240. The cable 1110 can typically carry frequencies for example from approximately Oto 8 GHz. The cable 1110 can be short or long. The UED 1112 has the processing power (i.e., CPU, baseband, modem, etc.) to handle the received signal and send signals to and from the antenna array 240. It also may contain communication modules such as WiFi radio, LTE/LTE-AILTE-U/LAA, and/or Zigbee. The UE 1112 can act as a small cell or WiFi Access Point. The UE 1112 can contact the user to the outside communication tower 1002 through the antenna array 240.

Figure 12:
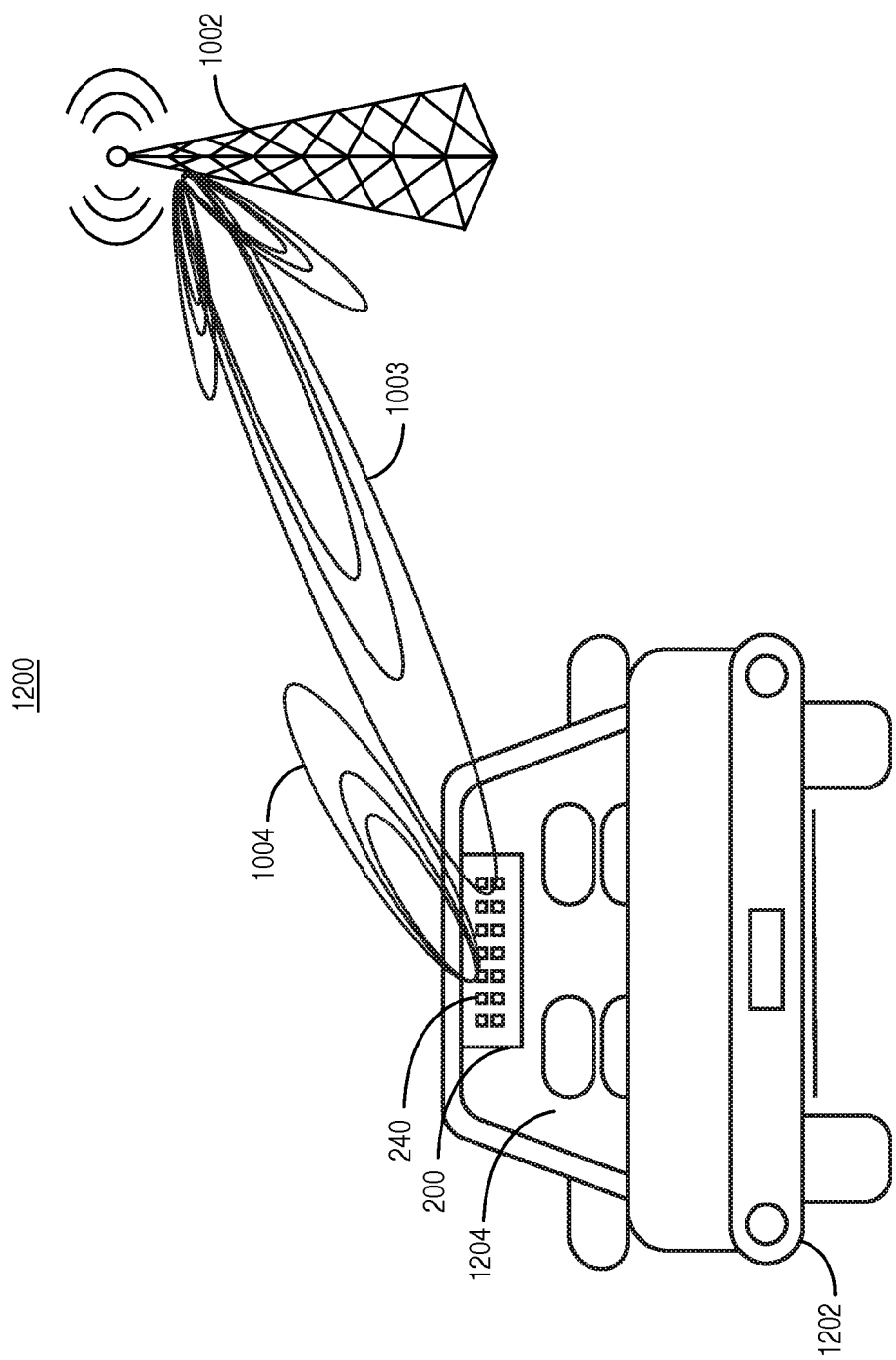
FIG. 12 shows an operating environment 1200 in which a communication tower 1002 communicates through mm wave signals 1103 and 1104 back and forth to and from a PCCC 200 with an antenna array 240 mounted in a vehicle 1202 on the glass 1204 through an adhesive.

FIG. 12 shows an alternative operating environment 1200 in which a communication tower 1002 communicates through mm wave signals 1003 and 1004 back and forth with a PCCC 200 (or PCCC 12020) with an antenna array 240 mounted in a vehicle 1202 on the glass 1204 through an adhesive such as suction cups. Alternatively, the glass 1204 could be manufactured with the components of the PCCC 200 (or PCCC 12020) built in.

Figure 13A:
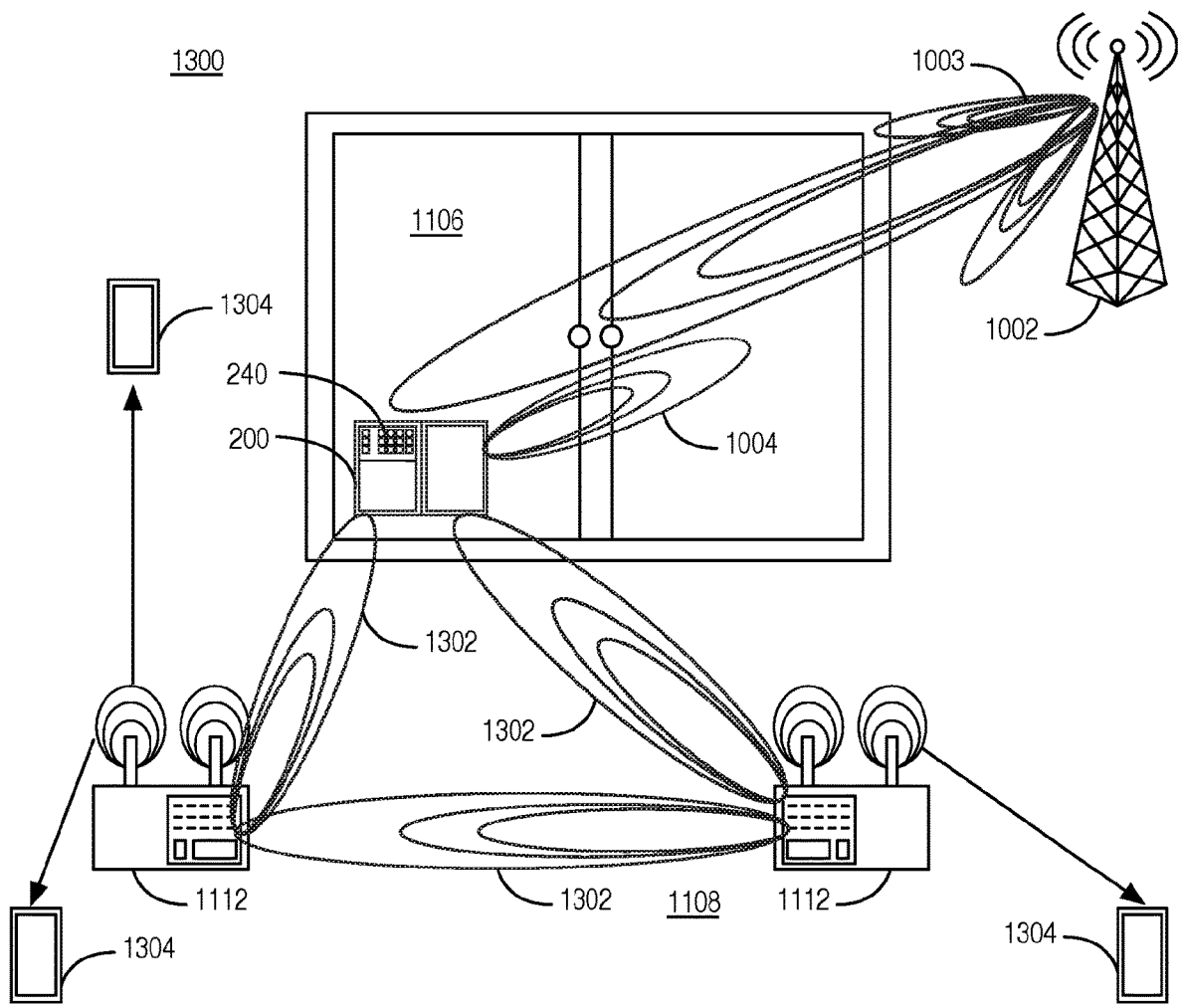
FIG. 13A shows an operating environment 1300 in which user equipment device 1112 has a PCCC 200 (e.g., mounted or integrated) so that PCCCs 200 can communicate with each other wirelessly using mm waves 1302
Figure 13B:
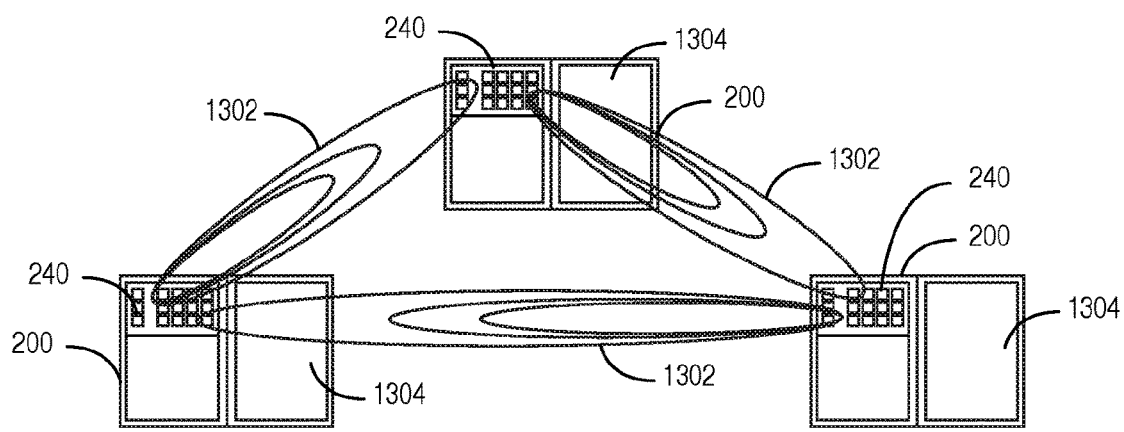
FIG. 13B illustrates a phone 1304 physically connected with a PCCC 200 (e.g., mounted or integrated) so that two PCCCs 200 can communicate with each other wirelessly.

FIG. 13A shows an alternative operating environment 1300 in which user equipment 1112 can further have a PCCC 200 mounted or integrated so that PCCCs 200 (or 12020) (in this case 3 PCCCs) can communicate with each other wirelessly using mm waves 1302. A first PCCC 200 could communicate with a plurality of PCCCs 200 at the same time or different times using beam forming, multiple input/multiple output (MIMO), massive MIMO, or the like. UED 1112 can then turn the mm waves 1302 in order to wirelessly communicate with mobile communication devices such as phones, tablets, etc. 1304. In FIG. 13B a phone 1304 can have a PCCC 200 (or 12020) connected (e.g., mounted or integrated), so that 2 PCCCs 200 could communicate with each other wirelessly for device to device communication. One PCCC 200 could communicate with a plurality of PCCCs 200 at the same time or different times using mm waves 1302 with beam forming, MIMO, massive MIMO, or the like.

Figure 14A:
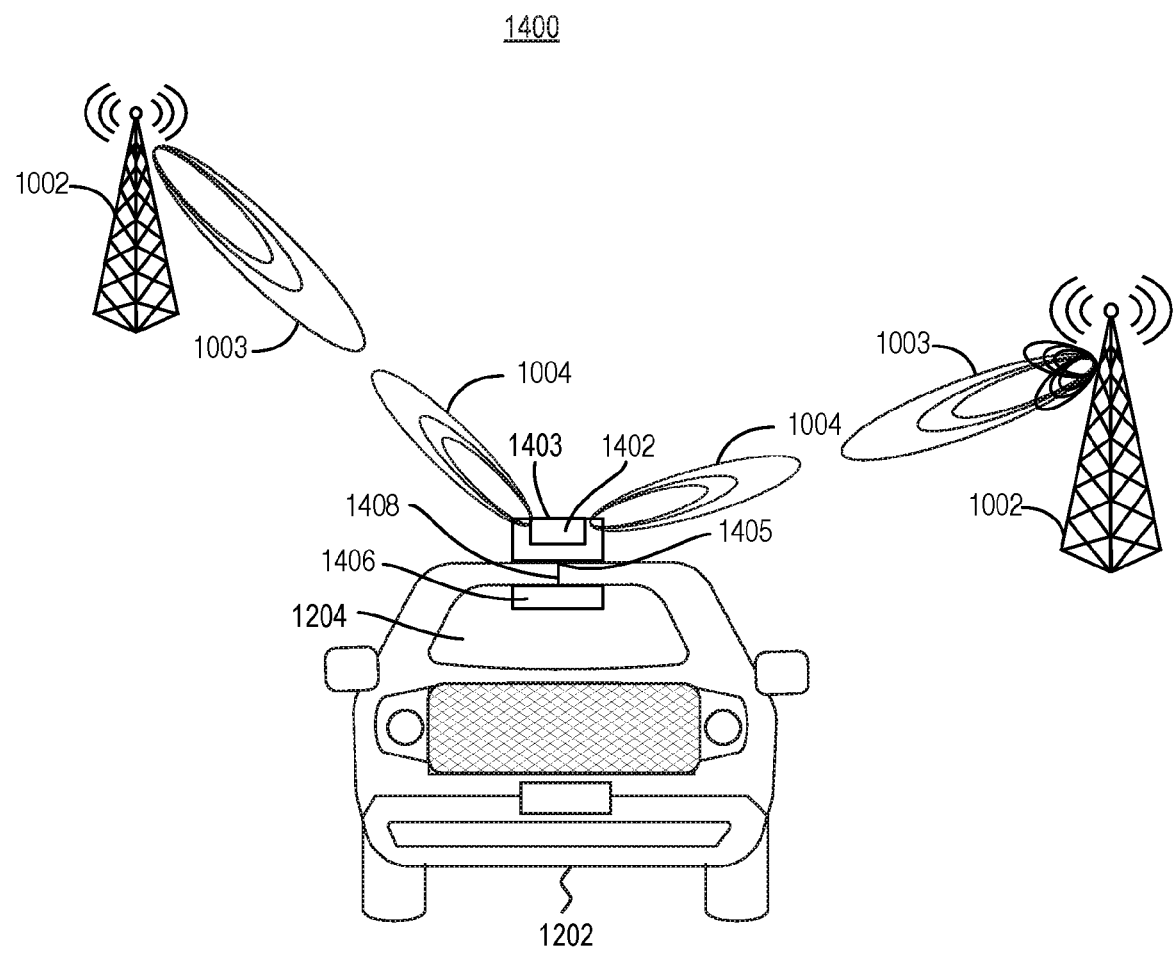
FIG. 14A shows an alternative operating environment 1400 in which a communication tower 1002 communicates through mm wave signals 1003 and 1004 back and forth with an antenna array 1402 mounted on an antenna panel 1403.

FIG. 14A shows an alternative operating environment 1400 in which a communication tower 1002 communicates through microwave and mm wave signals 1003 and 1004 back and forth with an antenna array elements (or "array" or "antenna array") 1402 mounted on antenna panel 1403. The array 1402 provides a personal cloud to the user and access to a wireless network (such as 3G, 4G, 5G, WiFi, SuperWifi, and similar technologies). As discussed above, new wireless and fixed standards keep pushing the operating frequencies into the microwave and millimeter (mm) wave spectrum (e.g., 28 GHz, 40 GHz, 60 GHz, 70 GHz, 100 GHz) and it becomes harder and harder (due to higher penetration loss and path loss) to get the signal inside buildings, houses, vehicles 102, and even mobile phones. The disclosed embodiments described herein help to make microwave and mm wave signal penetration possible. Antenna array 1402 can be a low cost antenna array made up of cells (or elements) in an N×N array (e.g. 2×2, 2×2, 4×4, 8×8, or the like) or an M×N array (e.g., 1×4, 2×4, 2×5, 2×8, or the like). The array 1402 and antenna panel 1403 could be circuit boards, the could be a chip antenna on the circuit boards, or they could be a multilayer antenna on the circuit boards. The antenna array 1402 can be used to increase the gain of the signal 1004, can be used for beam forming and beam steering, phase shifting, and/or gesture tracking. The antenna array 1402 may be coupled to and controlled by user equipment (UE) 1406 (such as a mobile communication device) wirelessly, through physical contact or through a connector (e.g., cable or electrical link(s)) 1408 running through the outer surface of vehicle 1202 (including through glass 1204).

Antenna array 1402 and antenna array panel 1403 may be configured in a plurality of ways. Antenna array 1402 may be made up of cells in an N×N or M×N array configuration as discussed above. The array panel 1403 may made of a low-cost material and a number of different substrates could be used each having their own fabrication tolerances and electrical and mechanical properties. The antenna array panel 1403 can be made of an Arion CLTE-XT (PTFE ceramic), a Rogers RT 5880/RO 3003 (PTFE glass fiber), a Rogers Liquid Crystal Polymer (LCP), a low temperature cofired ceramic (LTCC), a Parylene N dielectric, a polytetrafluoroethylene (PTFE) ceramic, a PTFE glass fiber material, a silicon material, a Gallium Arsenite (GaAs) material, an Alumina material, a Teflon material, a Duroid material or any other material that can produce thin (about 2-4 mils in thickness) metallized layers. In one embodiment, the layers may be stacked to form a multi-layer array architecture. With the antenna array 1402 printed on a thin film material, microwave and mm wave signals can penetrate through any object efficiently and at low cost.

In operating environment 1400, antenna array 1402 allows user equipment 1406 to communicate with communication towers (e.g., cell tower, base station or the like) 1002. Communication towers 1002 and antenna array 1402 could communicate with each other using, for example, time domain (TDD) or frequency domain signals (FDD). Downlink signal (or beam) 1003 coming from communication tower 1002 and uplink signal (or beam) 1004 coming from array 1402 are formed and steered to allow microwave and mm wave signal communications between the array 1402 and communication towers 1002. The antenna array 1402 may be located by communication towers 1002 using Global Positioning Satellite (GPS) technology or by 3G/4G/5G technology. Beams 1003 and 1004 may operate in the range of approximately 3 GigaHertz (GHz) to approximately 100 GHz or even higher. Typically, beams 1003 and 1004 will operate approximately in a range of plus or minus (+/−) 12% of mmwave frequency signals such as 24 GHz, 28 GHz, 39 GHz, 60 GHz, and/or 77 GHz (e.g., for 24 GHz the signal would range from approximately 21.12 GHz to approximately 26.88 GHz). Alternatively, mmWave beams 1003 and 1004 can operate in the following ranges: approximately 3.3 GHz to approximately 3.4 GHz; approximately 3.4 GHz to approximately 3.6 GHz; approximately 3.6 GHz to approximately 3.8 GHz; approximately 5.11202 GHz to approximately 5.925 GHz; approximately 24.25 GHz to approximately 27.5 GHz; approximately 31.8 GHz to approximately 33.4 GHz; approximately 37.0 GHz to approximately 40.5 GHz; approximately 40.5 GHz to approximately 42.5 GHz; approximately 42.5 GHz to approximately 43.5 GHz; approximately 45.5 GHz to approximately 47 GHz; approximately 47.0 GHz to approximately 47.2 GHz; approximately 47.2 GHz to approximately 1202.2 GHz; and approximately 1202.4 GHz to approximately 52.8 GHz.

Antenna array 1402 may be located at any point on the vehicle 1202 including the glass 1204 (and may be printed into or attached by suction cups to the glass 1204 in an alternative embodiments). The mm waves 1003 sent from the communication towers 1002 can be received at antenna array 1402 and then down converted in communication device 1406 to lower frequency signals (e.g., approximately 2 GHz, 5 GHz, 8 GHz or the like). In some embodiments, these lower frequency signals are forwarded from array 1402 through connector 1408 which goes through the outer layer of the vehicle 1202 to the user equipment device (or a plurality of user equipment devices) 1406. The antenna array 1402 can also send signals wirelessly to user equipment device 1406 (e.g., using 802.11ad and/or 802.11ax). User equipment device 1406 located in the vehicle 1202 has the ability to forward the signal through wireless signals (which typically are at different frequencies such as WiFi, Bluetooth, Zigbee, etc.) to a plurality of devices such as phones, tablets, and/or televisions which may be located in the vehicle 1202. Wired connector 1408 not only carries the RF signals received and sent to and from the antenna array 1402 but it may also provide control signals and power supply for the antenna array 1402. The connector 1408 can typically carry frequencies for example from approximately 0 to 8 GHz. The cable 1408 can be short or long. The UE 1406 has the processing power (i.e., CPU, baseband, modem, etc.) to handle the received signal and send signals to and from the antenna array 1402. It also may contain communication modules such as WiFi radio, LTE/LTE-AILTE-U/LAA, and/or Zigbee. The UE 1406 can act as a small cell or WiFi Access Point. The UE 1406 can contact the operator of the vehicle 1202 to the outside communication towers 1002 through the antenna array 1402.

Figure 14B:
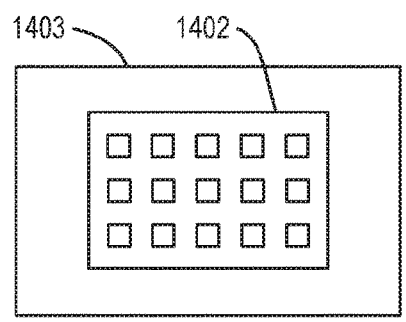
FIG. 14B is a planar view of one embodiment of the antenna array 1402 mounted on an antenna panel 1403.
Figure 14C:
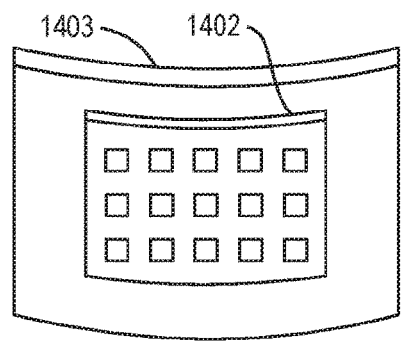
FIG. 14C is top view of an alternative embodiment of FIG. 14B in which the antenna panel 1403 and antenna array 1402 is bendable.
Figure 14D:
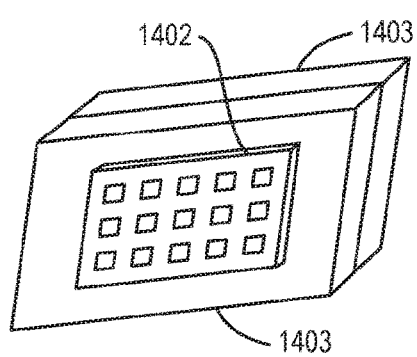
FIG. 14D is a perspective view and FIG. 14E a top view of two antenna arrays 1402 mounted on panels 1403 arranged in a back to back configuration.
Figure 14E:
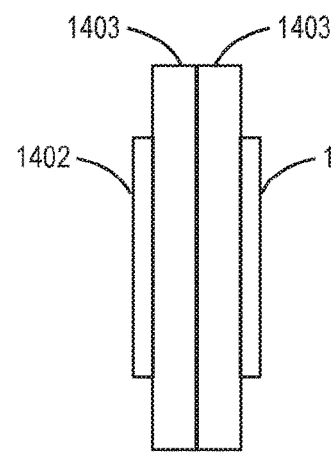
FIG. 14F is top view of an alternative embodiment of FIGS. 14D and 14E in which the antenna panels 1403 and antenna arrays 1402 are bendable.
FIG. 14G is a perspective view and FIG. 14H is a top view of three antenna arrays 1402 mounted on the exterior side of corresponding panels 1403 and arranged in a triangular configuration to improve the 360 degree reception.
FIG. 14I is a perspective view of four antenna arrays 1402 mounted on the exterior side of four panels 1403 to also improve the 360 degree reception.
FIG. 14J is a perspective view of six antenna arrays 1402 mounted on the exterior sides of panels 1403.
FIG. 14K shows a perspective view and FIG. 14L a top view of a circular antenna array 1402 mounted on the exterior of circular antenna panel 1403 to obtain 360 degree coverage.
FIG. 14M is a side view and FIG. 14N is a top view of a dome shaped antenna panel 1403 with an antenna array 1402 on top to obtain 360 degree coverage.
Figure 14F:
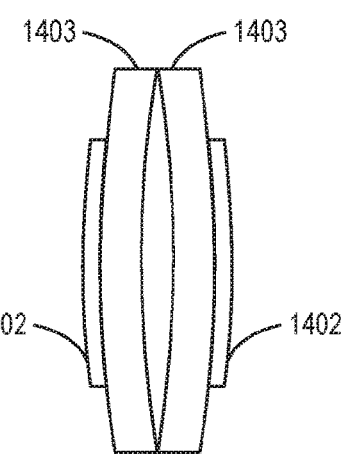
Figure 14G:
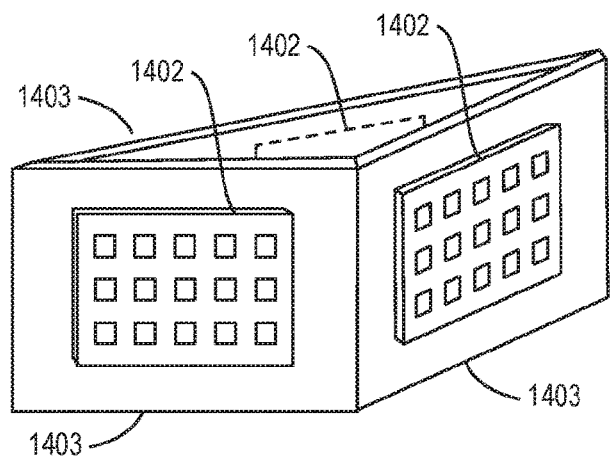
Figure 14H:
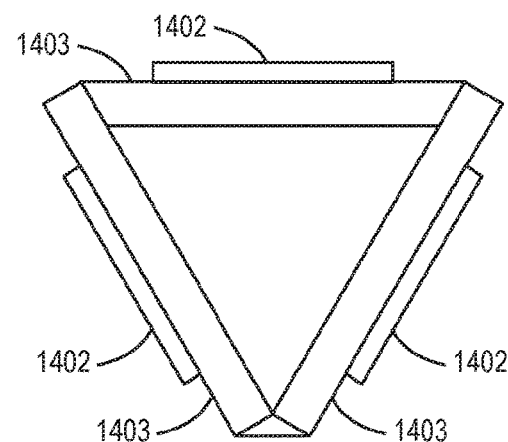
Figure 14I:
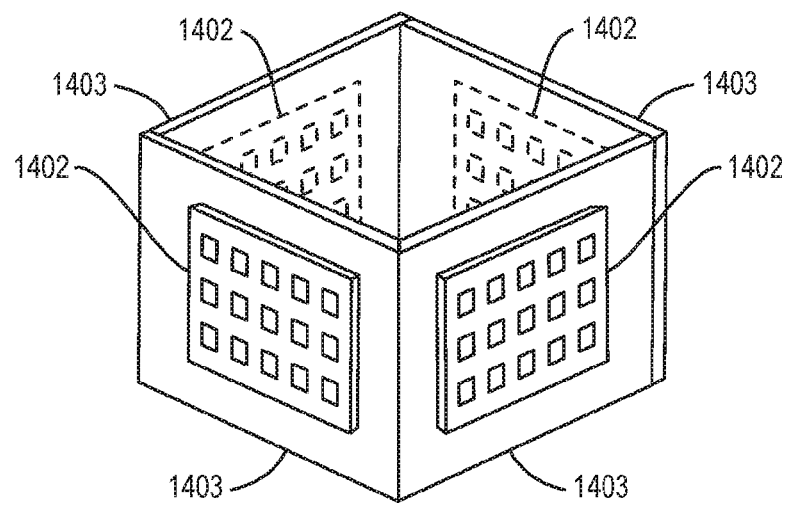
Figure 14J:
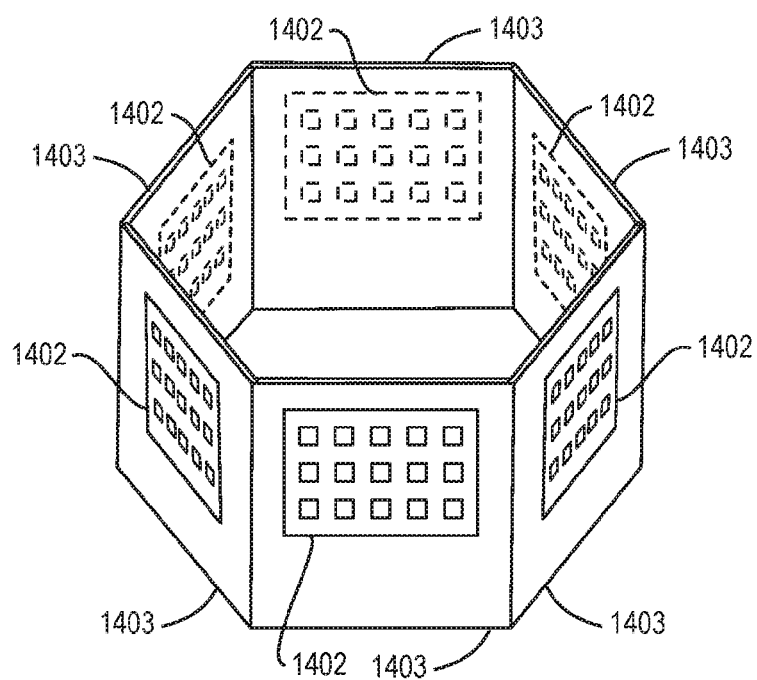
Figure 14K:
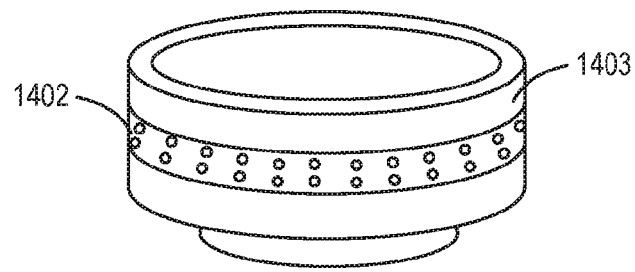
Figure 14L:
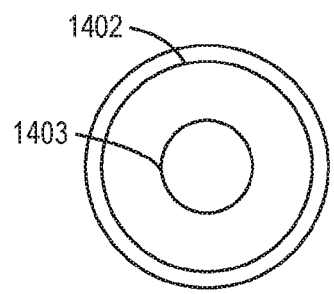
Figure 14M:
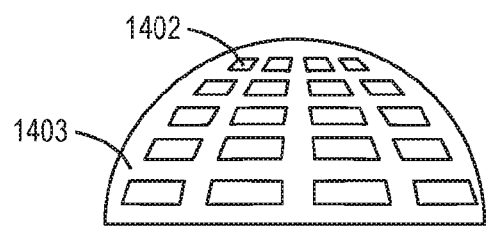
Figure 14N:
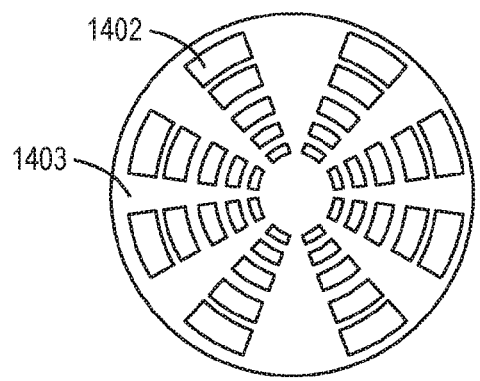

In one embodiment, antenna array 1402 may be a single array mounted on an antenna panel 1403 (e.g., a flat panel) at a platform 1405 on top of a vehicle 1202 (or any other exterior portion of the vehicle including glass 1204). In alternative embodiments, platform 1405 may have a plurality of arrays 1402 mounted on a plurality of panels 1403. The panels 1403 may be arranged in a vertical (or upright) manner compared to the platform 1405. The panels 1403 may be adjusted mechanically (or manually) or electronically to improve coverage. Coverage being the ability of the array 1402 to transmit and/or receive signals. The mechanical adjustment of panels 1403 may also depend on the phase of the arrays 1402 and the gain of the arrays 1402. Depending on the positioning of the panels 1403 to each other, coverage may extend in a range from greater than 0 degrees to 360 degrees. The term "surrounding" as used in herein means the coverage for the panels 1403 is greater than 180 degrees and up to and including 360 degrees. FIG. 14B is a planar view of one embodiment of the antenna array 1402 mounted on an antenna panel 1403. FIG. 14C is top view of an alternative embodiment of FIG. 14B in which the antenna panel 1403 and antenna array 1402 are bendable. In this case, the antenna panel 1403 may be made of a plastic material. FIG. 14D is a perspective view and FIG. 14E a top view of two antenna arrays 1402 mounted on panels 1403 arranged in a back to back configuration. This configuration allows for 360 degree transmission and reception of signals in the horizontal plane to and from tower 1002 (having a base station) and/or other cell towers. Each of the arrays 1402 is coupled to the communication device 1406. FIG. 14F is top view of an alternative embodiment of FIGS. 14D and 14E in which the antenna panels 1403 and antenna arrays 1402 are bendable. FIG. 14G is a perspective view and FIG. 14H is a top view of three antenna arrays 1402 mounted on the exterior side of corresponding panels 1403 and arranged in a triangular configuration to improve the 360 degree transmission and reception of signals in the horizontal plane. Each of the arrays 1402 is coupled to the communication device 1406. The arrays 1402 and panels 1403 may be configured in any polygonal shape such as the triangle, quadrilateral, pentagon, hexagon including up to and beyond decagons. FIG. 14I is a perspective view of four antenna arrays 1402 mounted on the exterior side of four panels 1403 to form a quadrilateral configuration with internal angles of 90 degrees (or approximately 90 degrees) and to improve the 360 degree transmission and reception of signals in the horizontal plane. Each of the arrays 1402 is coupled to the communication device 1406. FIG. 14J is a perspective view of six antenna arrays 1402 mounted on the exterior sides of panels 1403 to form a hexagon configuration. Each of the arrays 1402 is coupled to the communication device 1406. FIG. 14K shows a perspective view and FIG. 14L a top view of a circular antenna array 1402 mounted on the exterior of circular panel 1403 to obtain 360 degree coverage transmission and reception of signals in the horizontal plane. The circular configuration of array 1402 is attached to communication device 1406. FIG. 14M is a side view and FIG. 14N is a top view of a dome shaped antenna panel 1403 with an antenna array 1402 on top to obtain 360 degree transmission and reception signal coverage in the horizontal plane.

Figure 15A:
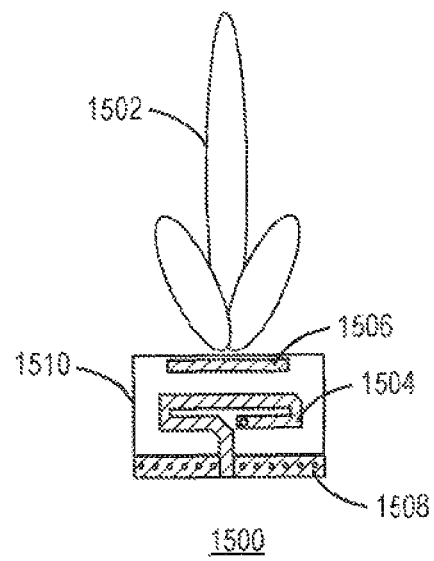
FIG. 15A shows an edge-emitting antenna (EEA) element 1500 for emitting electromagnetic waves 1502.

FIG. 15A shows an edge-emitting antenna (EEA) element 1500 for emitting electromagnetic waves 1502. The EEA element 1500 comprises a resonator 1504, one of more directors 1506, and a reflector 1508. The EEA 1500 may be constructed as metal on an antenna panel (e.g., PCB having dielectric layers) 1510 or as metal on a semiconductor die.

Figure 15B:
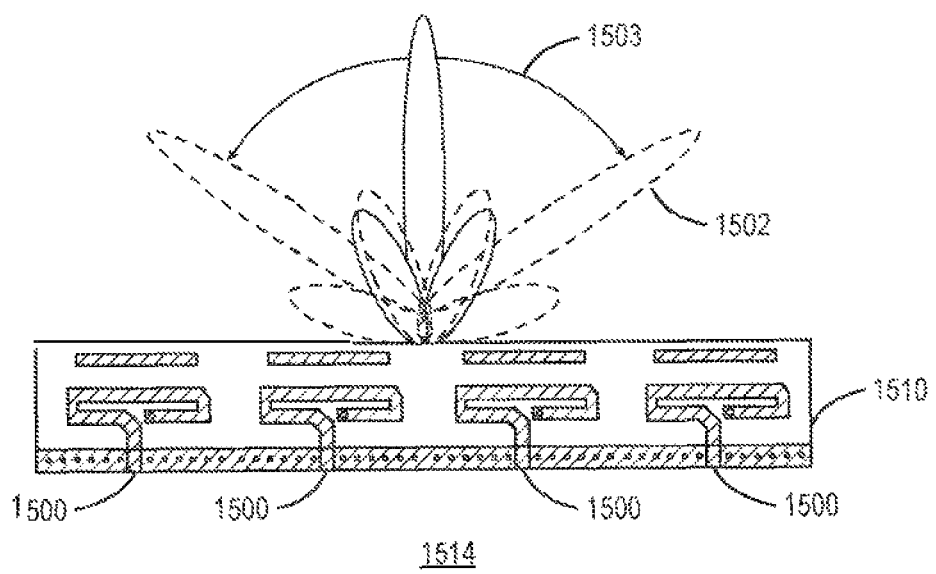
FIG. 15B shows an array 1514 of EEA's 1500 that can be used to enhance 1503 the strength of the electromagnetic wave 1502 transmitted in a selected direction.

FIG. 15B shows an array 1514 of EEA's 1500 on antenna panel 1510 that can be used to enhance the strength of the electromagnetic wave transmitted in a selected direction. The main radiating direction and pattern and the electromagnetic waves 1502 of an EEA array 1514 can be dynamically changed by changing the relative phases of RF signals being sent to the EEA elements 1500.

Figure 15C:
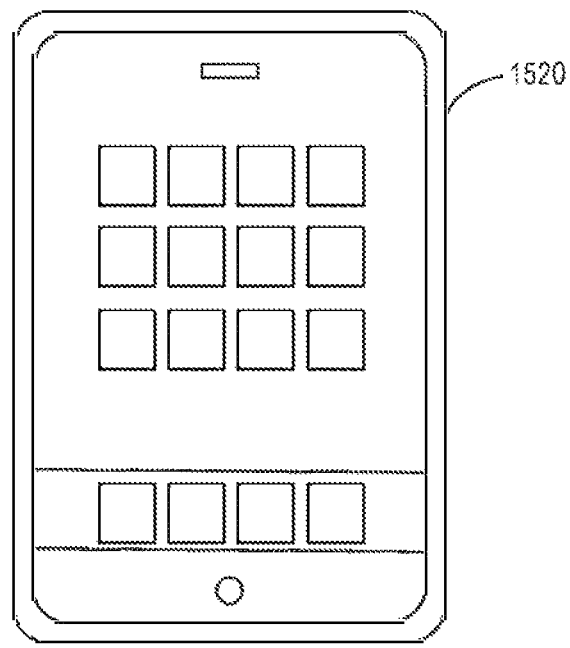
FIGS. 15C and 15D show arrays 1514 can be mounted at the edges or corners of a mobile device 1520 having a PCB panel 1510 such as smartphones, wireless tablets, and computers.
Figure 15D:
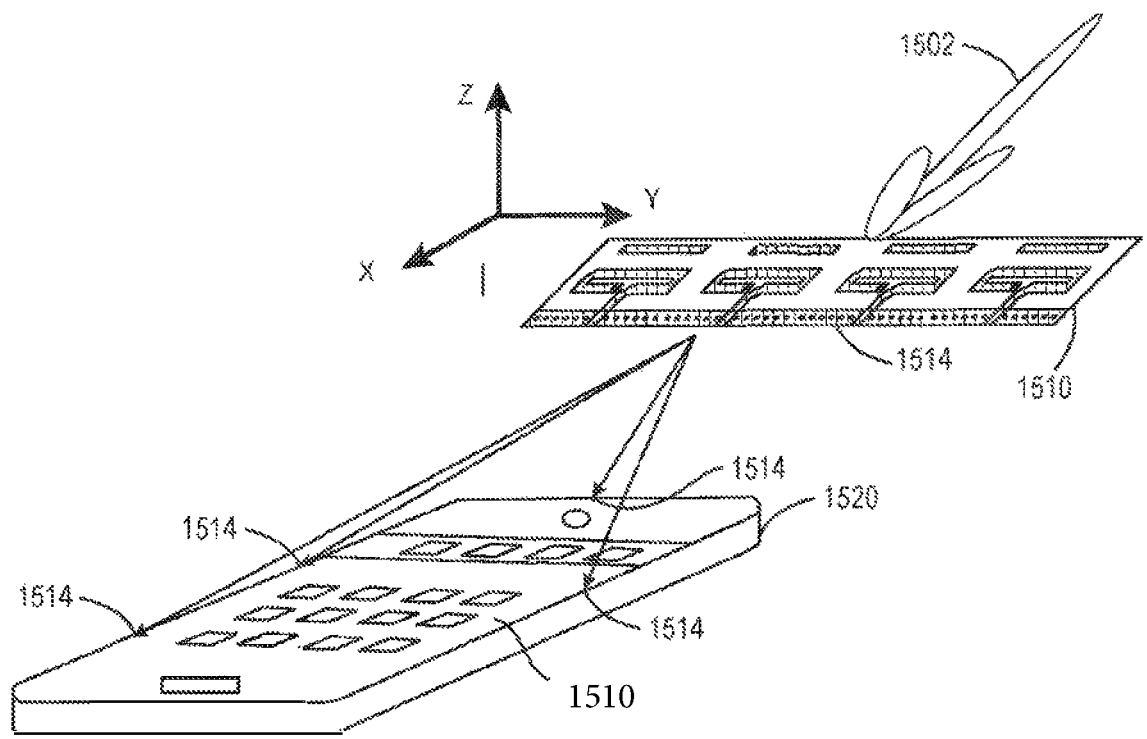

FIGS. 15C and 15D show arrays 1514 that can be mounted at the edges or corners of a mobile device 1520 having a PCB 1510 such as smartphones, wireless tablets, and computers. FIG. 15D is a perspective view showing electromagnetic waves 1502 of EEA array 1514 emitting radio frequency signals (e.g., microwave and mmwave signals) primarily on horizontal (X-Y) plane of the antenna panel 1510 or the semiconductor die. As shown in FIG. 15D, EEA array 1514 is mounted in the X-Y plane parallel to the face of PCB 1510 of a mobile device 1520 and the radio waves are emitting from the edges, sides or the corners of the mobile device 1520 advantageously. The radio waves are transmitted and received substantially in the X-Y plane of the antenna PCB panel 1510 of the array 1514 to avoid interference with other circuitry on the PCB 1510. EEA array 1514 can also be used to transmit RF to a preferred direction or to receive RF signals from a preferred direction, or to both transmit and receive RF signals to and from a preferred direction.

Figure 15E:
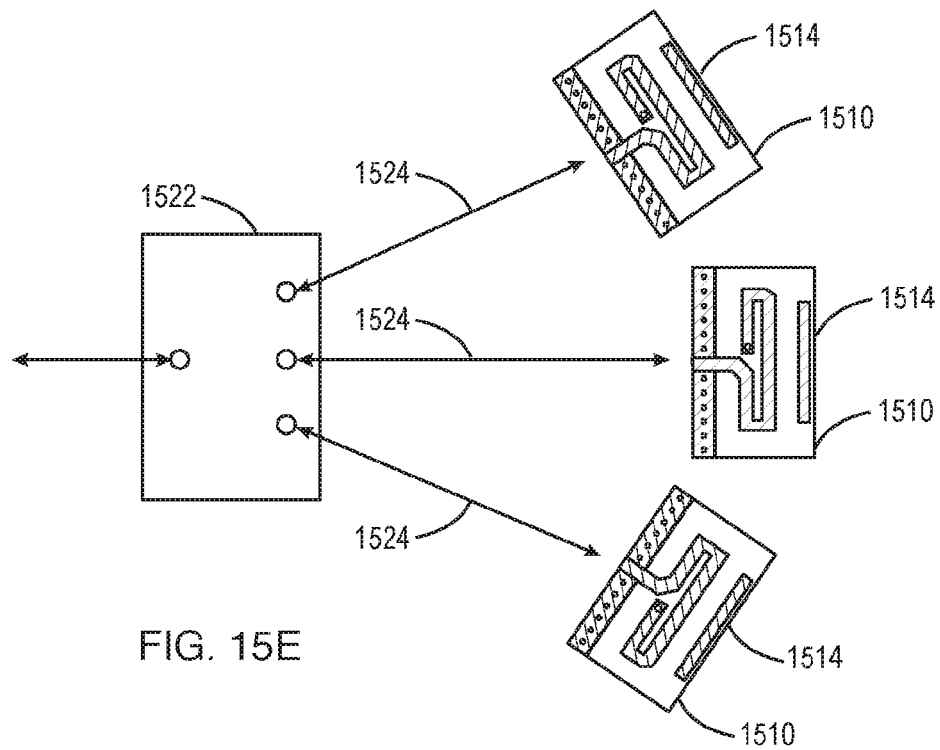
FIG. 15E shows EEA arrays 1514 (or could be individual EEA elements in an alternative embodiment) which could be arranged to have the primary radiation pointing to or from different directions.

FIG. 15E shows EEA arrays 1514 which could be arranged to have their primary radiation and reception pointing to or from different directions. FIG. 15E shows the EEAs arrays 1514 pointing, for example, in three different directions at different angles of coverage to improve the coverage range. EEA arrays 1514 can function independently or jointly and may be controlled by switch 1522 and receive and send signals through lines 1524. There can be a switch 1522 for RF signals 1524 to different EEA arrays 1514. RF switch 1522 can be used to select the antenna for a preferred direction.

Figure 15F:
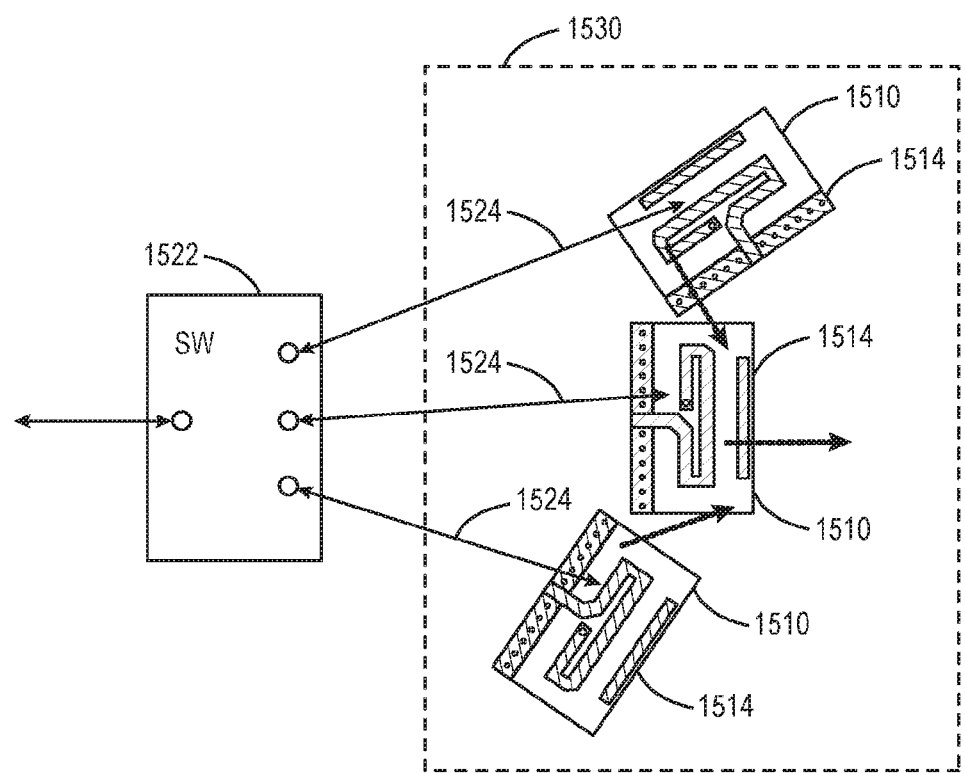
FIG. 15F shows EEA arrays 1514 (or could be individual EEA elements 1500 in an alternative embodiment) in a stack of multiple layers and be arranged to have its primary radiation pointing to or from different directions.

FIG. 15F shows EEA arrays 1514 formed in a stack of multiple layers 1530 and be arranged to have its primary radiation and reception pointing to or from different directions. EEA arrays 1514 can function independently or jointly. Each layer can be used to transmit, to receive, or both to transmit and to receive. Each layer could be combined to shape the electromagnetic wave beam 1502. Having EEA arrays 1514 pointing to different directions could eliminate phase shifters and complex computing. As discussed with FIG. 15E, EEA array 1514 layers can function independently or jointly and may be controlled by switch 1522 and receive and send signals through lines 1524. There can be a switch 1522 for RF signals 1524 to different EEA arrays 1514. RF switch 1522 can be used to select the antenna for a preferred direction.

Figure 15G:
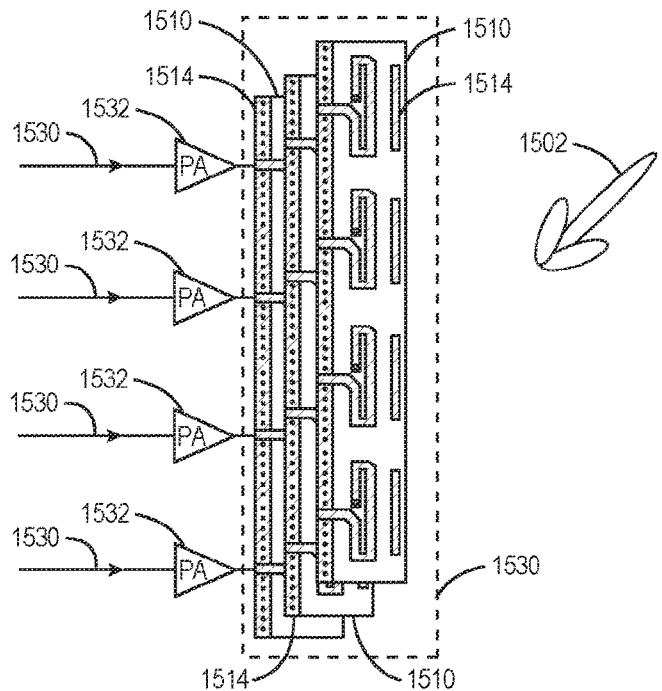
FIG. 15G shows a multi-layer antenna array 1530 made up of EEA arrays 1514 receiving signals 1530 through power amplifiers 1532 and transmitting electromagnetic wave RF signals 1502.

FIG. 15G shows a multi-layer antenna array 1530 receiving signals 1530 through power amplifiers 1532. Antenna arrays 1514 can be used for transmitting and receiving RF signals from selected directions.

Figure 15H:
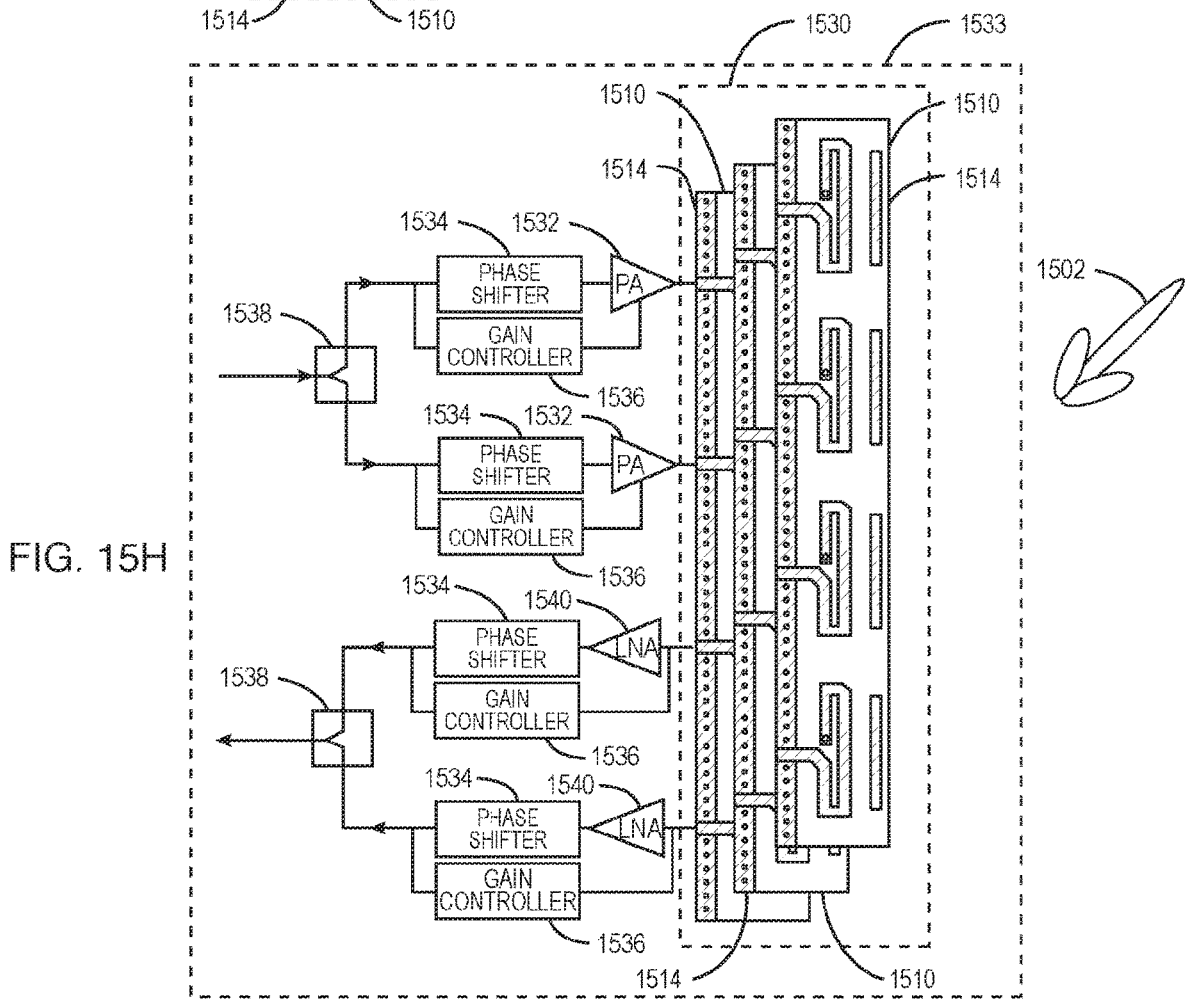
FIG. 15H shows a multi-layer antenna array 1530 made up of EEA arrays 1514 which is part of an antenna array module 1533 that can be used to transmit or to receive electromagnetic wave RF signals 1502.

FIG. 15H shows a multi-layer antenna array 1530 made up of EEA arrays 1514 which is part of an antenna array module 1533 that can be used to transmit or to receive RF signals (e.g., mmWave or microwave signals). The module 1533 includes circuitry necessary for RF communications such as power amplifiers 1532, phase shifters 1534, gain controllers 1536, splitters 1538, and low noise amplifiers 1540.

Figure 15I:
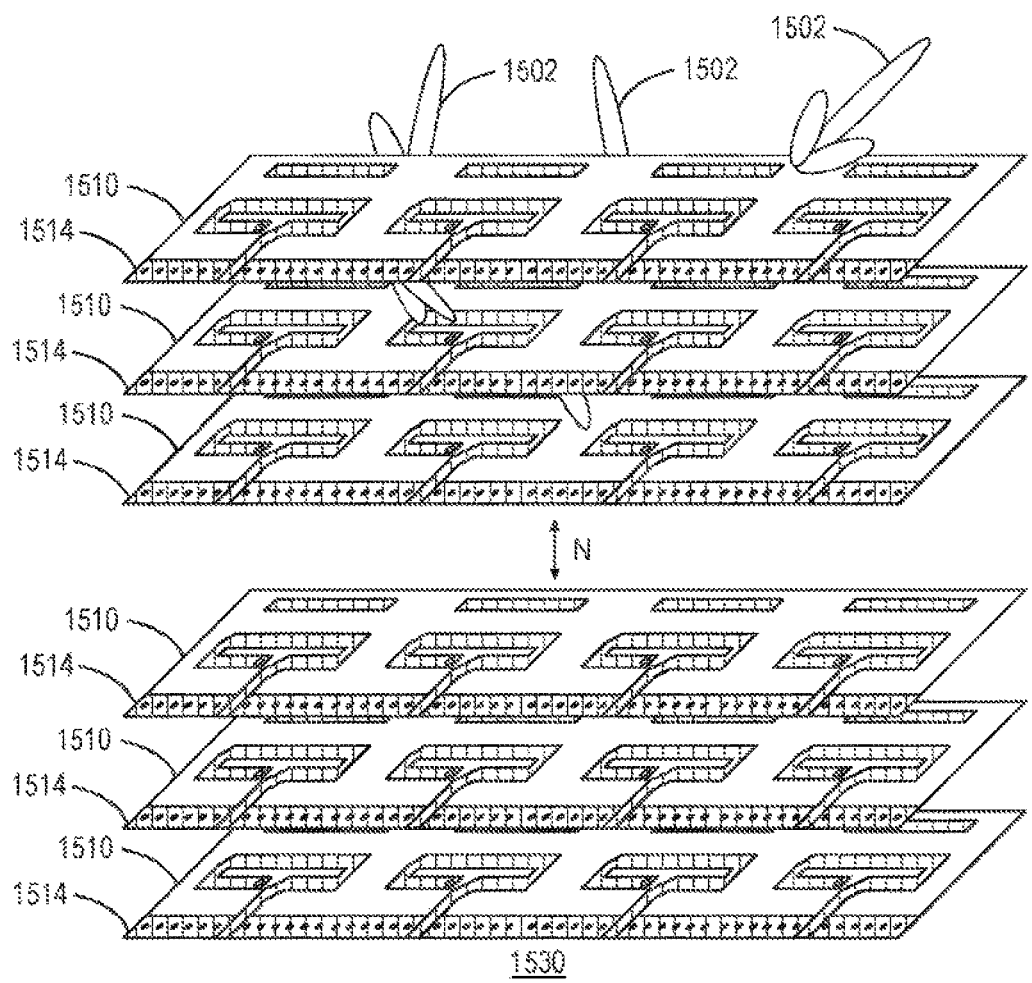
FIG. 15I shows a multilayer EEA array 1530 made up of N+1 array 1514 layers in a range of 2 to 10 or greater with each layer 1514 capable of functioning independently or jointly.

FIG. 15I shows that a multilayer EEA array 1530 could be made up of N+1 array 1514 layers in a range of 2 to 10 or greater with each layer 1514 capable of functioning independently or jointly.

Figure 15J:
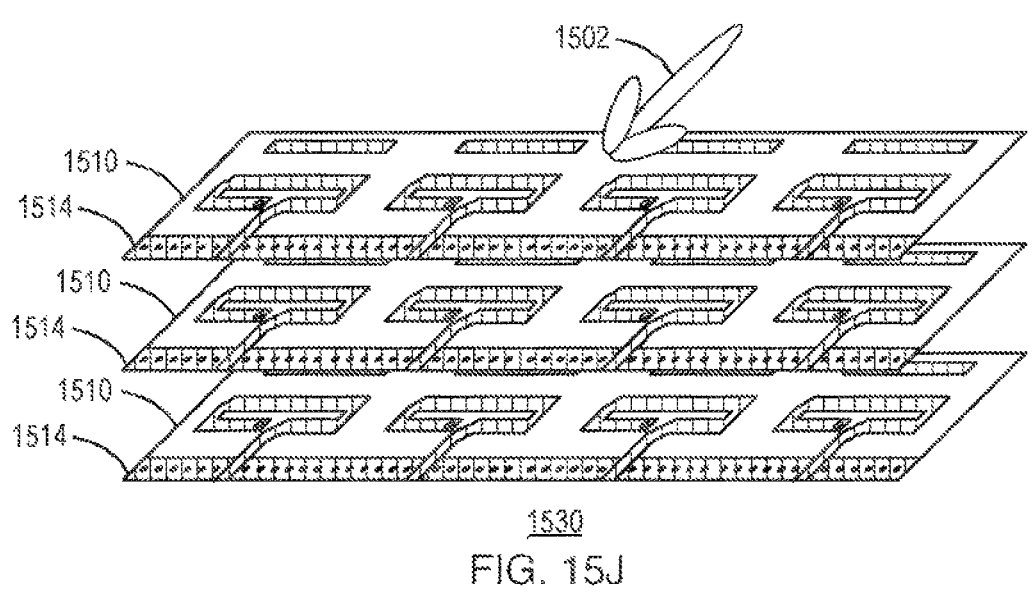
FIG. 15J shows that a multilayer EEA array 1530 could be configured so that each layer 1514 can function independently or jointly (e.g., operating at different frequencies).

FIG. 15J show that a multilayer EEA array 1530 could be configured so that each layer 1514 can function independently or jointly (e.g., at different frequencies). Each layer can be used to transmit, to receive, or both to transmit and to receive for preferred directions at different frequencies. Each layer 1514 could be combined to shape the electromagnetic beam 1502.

Figure 16:
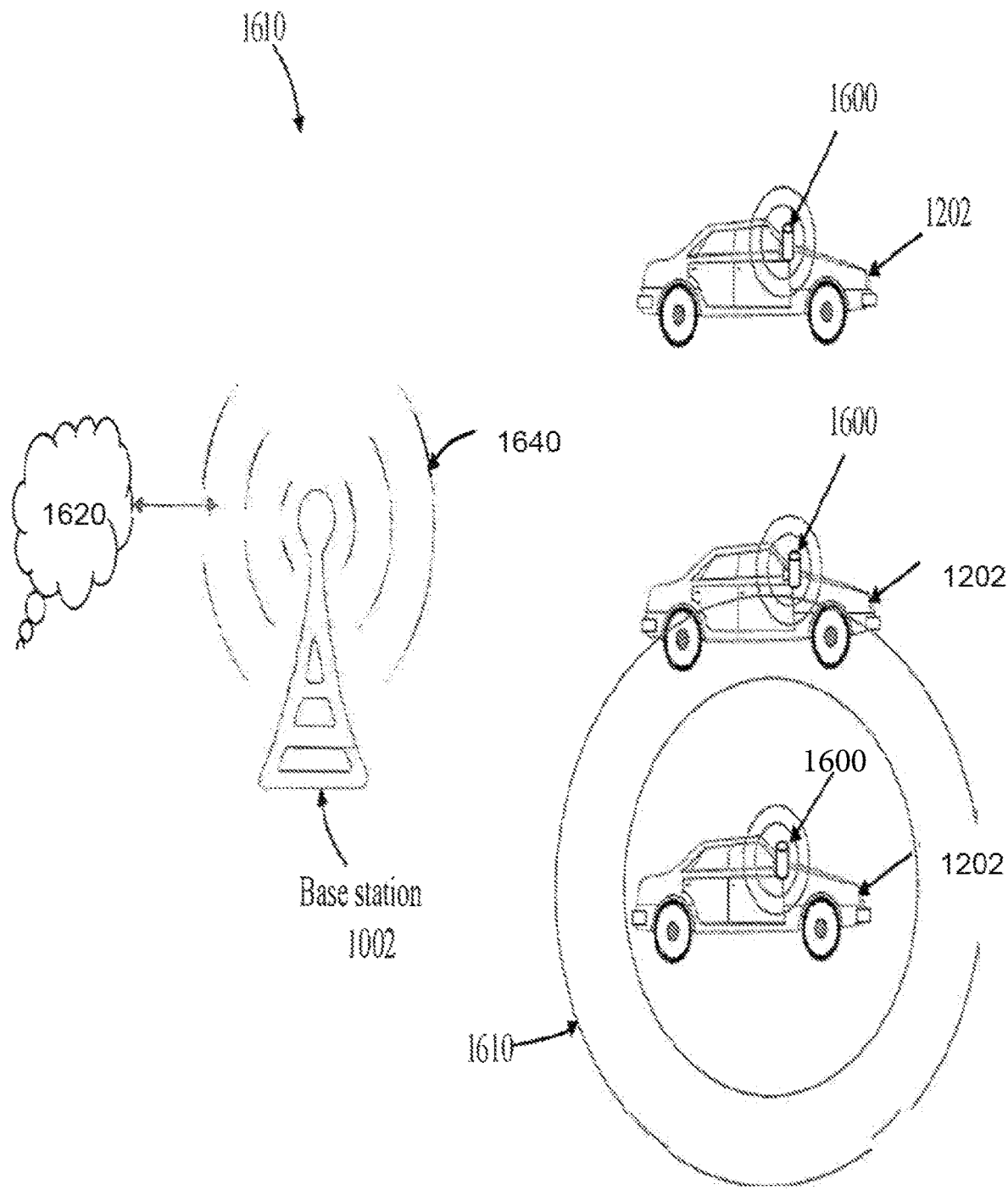
FIG. 16 is a block diagram showing short and long-rangewireless network systems comprising wireless hubs 1600.

FIG. 16 shows using the antenna arrays of FIGS. 15A-15J in a wireless hub (WH) 1600 in a wireless network 1610 which includes Internet (or cloud) 1620 and base stations 1002 that provide long-range wireless networks 1640. The long-range wireless networks 1640 can be terrestrial or satellite based wireless wide area networks. Examples of terrestrial based long-range wireless standards include 2G, 3G, 4G and 5G cellular networks and beyond, for example, Universal Mobile Telecommunications System (UMTS), WiMax, WiBro, 3GPP, GSM, WCDMA, LTE, LTE-Advanced or IMT-2000. Wireless hubs 1600 may be in vehicles 1202 located in the coverage area of the long-range wireless network 1640. The WHs 1600 may be attached to the vehicles or portable. The WHs 1600 can draw power from their respective vehicles 1202 and have wireless connections with the base stations 1002 and thus the Internet 1620 via long-range wireless network 1640. The vehicles 1202 can include almost any types of motor vehicles such as passenger cars, commercial trucks, buses, taxis, police cars, and delivery vehicles. The vehicles 1202 can be stationary or in motion with the WHs 1600 operating.

Vehicles 1202 are a platform for providing short-range wireless networks because of high ownership rates and the ubiquitous nature of motor vehicles in modern society. In the U.S. for example, the ownership rate of cars is seventy-eight cars per one hundred people. Cars are necessities for eighty-six out of every one hundred Americans.

Figure 17:
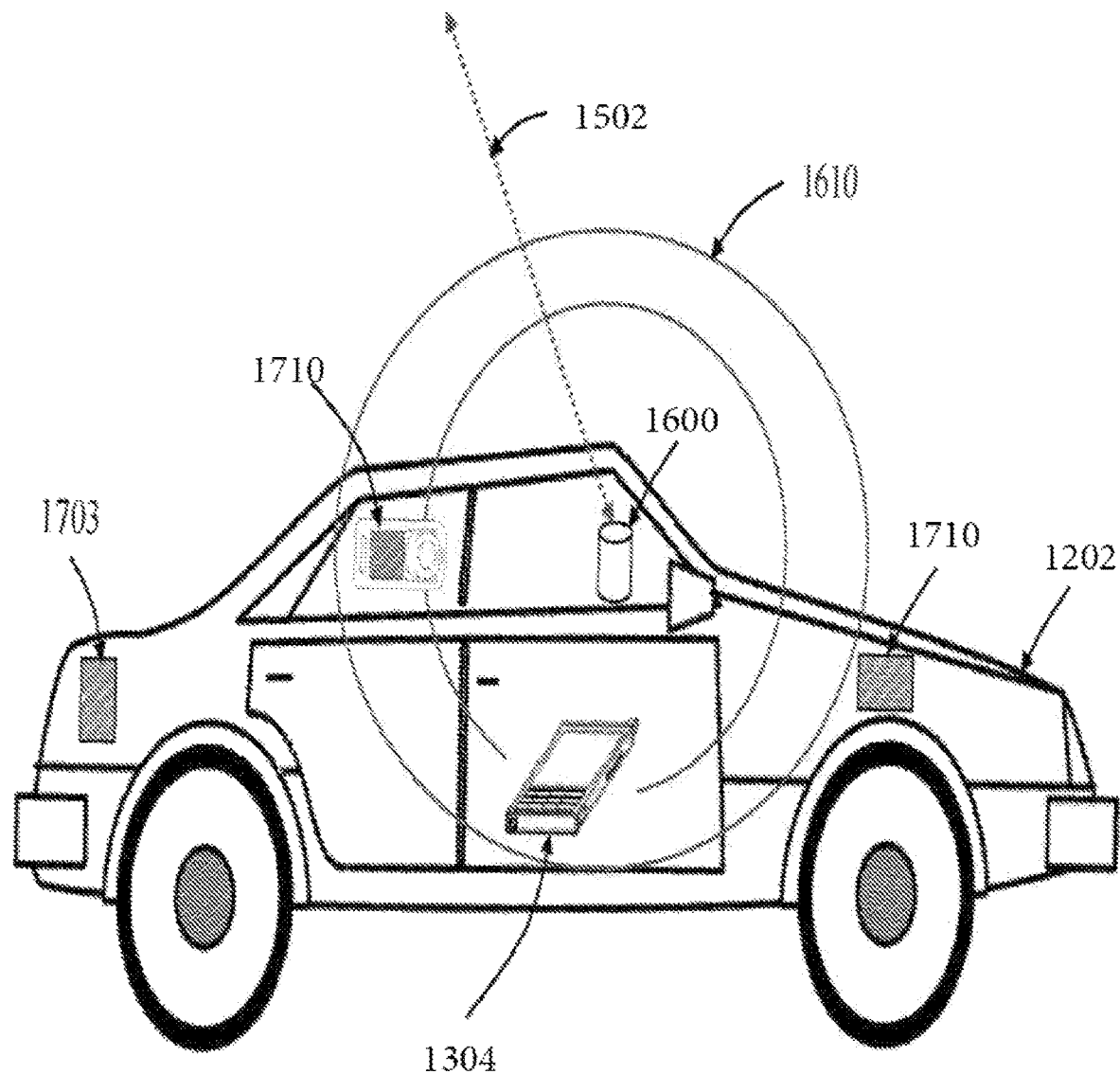
FIG. 17 is a schematic diagram showing a short-range wireless network 1610 enabled by a wireless hub in a vehicle.

Referring to FIG. 17, each WH 1600 can produce a short-range wireless network 1610 inside and around the vehicle in which the WH 1600 is located or installed. Examples of short-range wireless standards include WiFi (WLAN), Bluetooth™, and Zigbee. A vehicle 1202 often carries a number of electronic devices 1304, 1710 that are capable of connecting to short-range wireless networks, but these devices may not have the hardware or the subscription to connect to long-range wireless networks 1640. Examples of the electronic devices 1304 and 1710 may include laptops, tablet computers, smart phones, electronic readers, and portable media devices. The electronic devices 1710 may communicate in the short-range wireless networks 1610 with electronic devices 1710 located in other vehicles 1202.

Each WH 1600 also produces a long range signal 1502 that connects to the base station 1002. The reference numerals 1502 and 1640 will be used interchangeably herein to indicate the long range signal and/or long range network.

In some embodiments, the vehicle 1202 can be installed with a personal server 1703 that is in short-range wireless communication with the WH 1600 through short range wireless network 1610. The personal server 1703 can include data storage, applications processors, and graphics processors. The personal server 1703 can be plugged into a cigarette lighter outlet or other connections within the vehicle 1202, but also includes more memory and faster processors than typical electronic devices 1710. The bulk of the data from the electronic devices 1710 can be stored in the personal server 1703, which can reduce data traffic through the long-range wireless networks 1620 to the Internet 1620. This personal server 1703 can also be accessed by connecting first to the WH 1600 via long-range network 1640 and having the WH 1600 direct data through 3G, 4G and/or 5G networks. In this way, a wireless device not in range of the WH 1600 can access data on the personal server 1703 via the long-range wireless network 1640, through the WH 1600 and the short-range wireless network 1610.

Figure 18A:
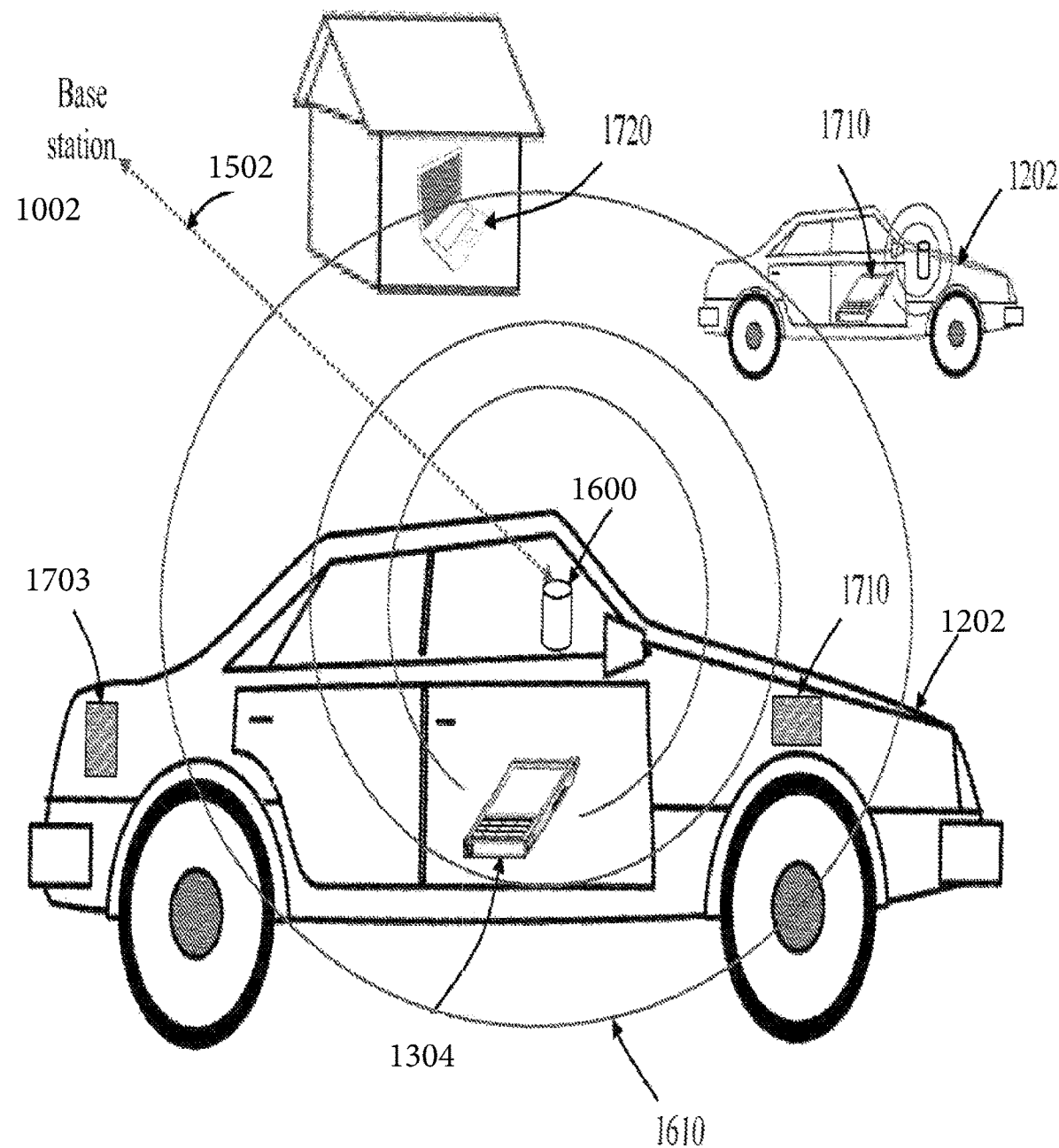
FIG. 18A is schematic diagram showing a short-range wireless network 1610 enabled by a wireless hub 1600 around a vehicle.

Referring to FIG. 18A, the WH 1600 on a vehicle 1202 can provide the short-range wireless network 1610 for an electronic device 1710 on a vehicle 1202 nearby or a stationary electronic device 1710 in a house, a building, or the ground. The short-range wireless network 1610 allows the electronic devices 1710 to connect to the Internet 1620 (FIG. 16) and to each other without access to long-range wireless network 1640.

Figure 18B:
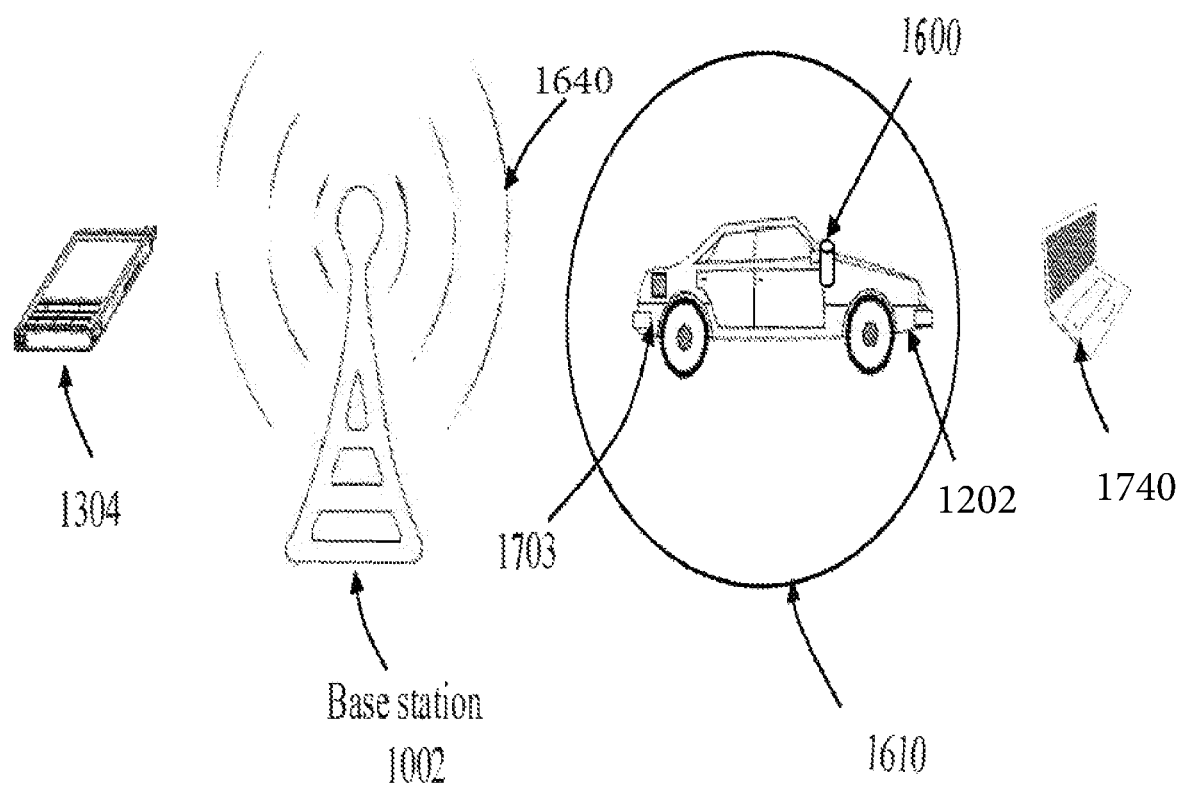
FIG. 18B is schematic diagram showing a wireless network 1610 enabled by a wireless hub 1600 around a vehicle.

In some embodiments, referring to FIG. 18B, mobile device 1304 has access to long-range wireless network 1640 and can connect to the WH 1600 in vehicle 1202 which can further access or control wireless device 1740 connected to the WH 1600 via the short-range wireless network 1610. For example, mobile device 1304 connected to the long-range wireless network 1640 can control another mobile device or access data on the personal server 1703, via the WH 1600, from a location remote from the vehicle 1202. This process could also work in reverse, with the device 1740 connected to the WH's 1600 short-range wireless network controlling the device 1304 connected to long-range network 1640. An advantageous feature of the presently disclosed system is that people are within a short distance from their vehicles 1202 most of the time. For example, cars are usually parked nearby when people are at home, at work, or go shopping. Thus, a vehicle based WH 1600 can provide ubiquitous coverage during peoples' daily activities.

In some embodiments, electronic devices 1304 or 1710 in the short-range wireless network 1610 can be used by any user in the vehicle 1202 and can share computing tasks. In some embodiments, WH 1600 on a vehicle 1202 can communicate with a WH 1600 on another vehicle 1202 to create a mesh network for the electronic devices 1304 or 1710 to share computing and memory resources.

Figure 19:
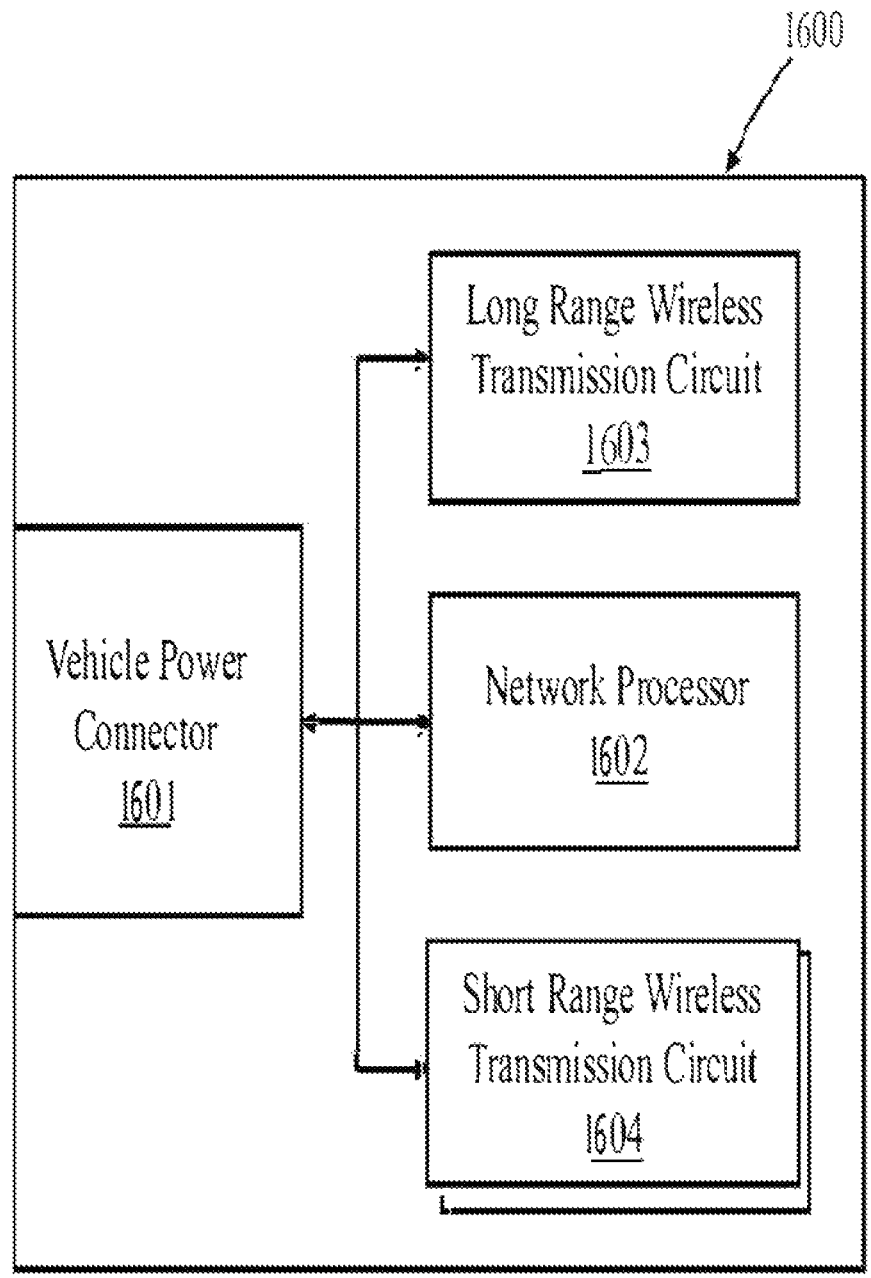
FIG. 19 is a system block diagram of a wireless hub 1600.

Referring to FIG. 19, a WH 1600 can include the following basic functions: a vehicle power connector 1601, a network processor 1602, a long range (or wide-area) transmission circuit 1603, and one or more short-range wireless transmission circuits 1604 for different short-range wireless communication standards. The vehicle power connector 1601 allows the WH 1600 to draw power from a vehicle battery. The long range transmission circuit 1603 is responsible for data transmission and reception with the long range wireless network 1640 (e.g. 3G, 4G or 5G networks). The long range wireless signals 1502 (discussed above in reference to FIGS. 15A-15J) and the short range signals 1610 may be mmWave and/or microwave signals. The RF signal beams 1502, 1610 (shown in FIG. 17) can operate in the following ranges: 400 MHz to 1 TerraHertz. Typically, beams 1502, 1610 will operate approximately in a range of plus or minus (+/−) 12% of mmWave frequency signals such as 24 GHz, 28 GHz, 39 GHz, 60 GHz, and/or 77 GHz (e.g., for 24 GHz the signal would range from approximately 21.12 GHz to approximately 26.88 GHz). For instance the RF signals 1502, 1610 can be: approximately 3.3 GHz to approximately 3.4 GHz; approximately 3.4 GHz to approximately 3.6 GHz; approximately 3.6 GHz to approximately 3.8 GHz; approximately 5.11202 GHz to approximately 5.925 GHz; approximately 24.25 GHz to approximately 27.5 GHz; approximately 31.8 GHz to approximately 33.4 GHz; approximately 37.0 GHz to approximately 40.5 GHz; approximately 40.5 GHz to approximately 42.5 GHz; approximately 42.5 GHz to approximately 43.5 GHz; approximately 45.5 GHz to approximately 47 GHz; approximately 47.0 GHz to approximately 47.2 GHz; approximately 47.2 GHz to approximately 1202.2 GHz; and approximately 1202.4 GHz to approximately 52.8 GHz. The short-range wireless transmission circuits 1604 are responsible for providing the short-range wireless networks 1610 (e.g. WiFi, Bluetooth, etc.) for data communications with the electronic devices 1710, 1740 (FIGS. 16-18B).

Figure 20:
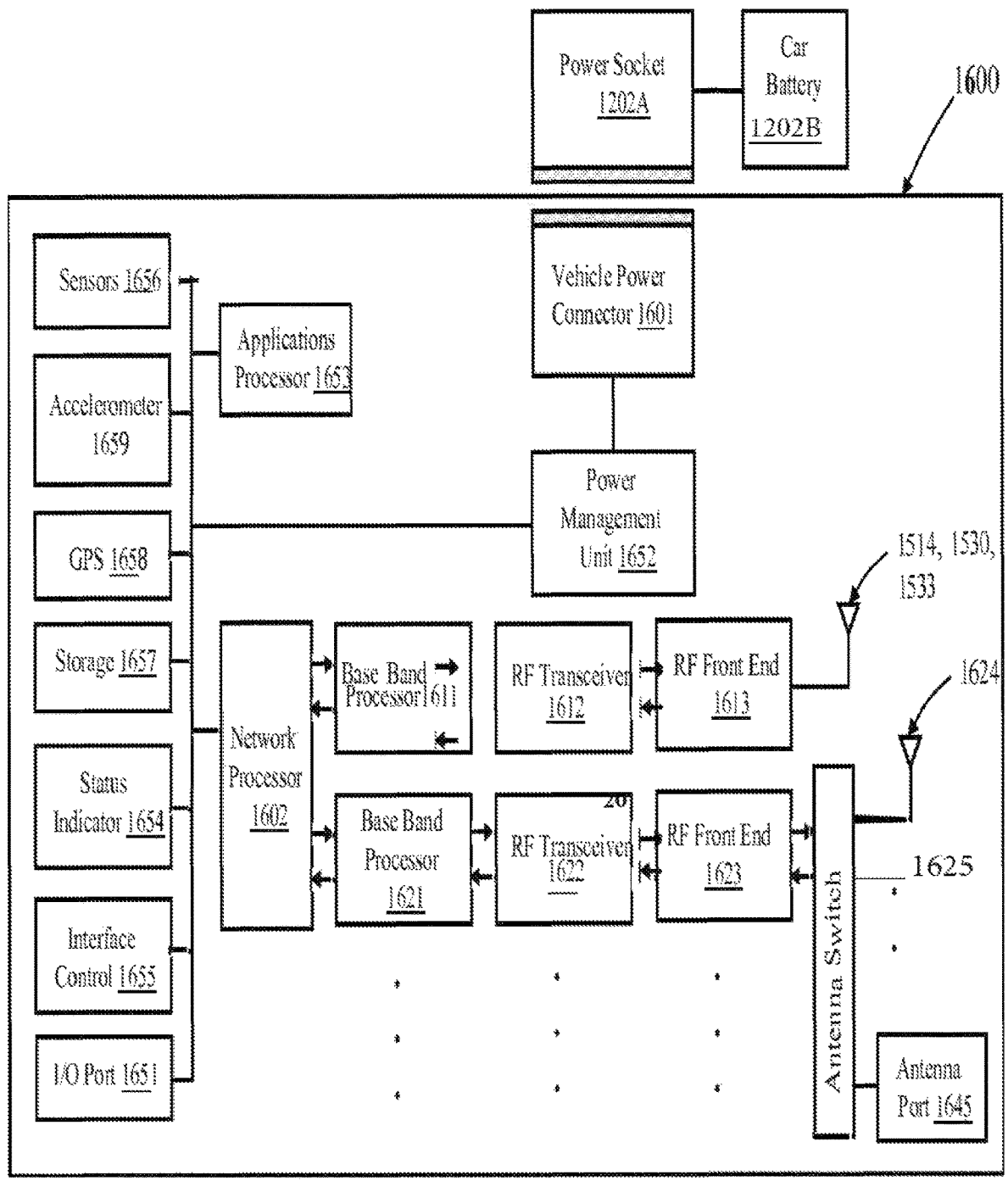
FIG. 20 is a detailed scematic diagram of a wireless hub 1600.

Referring to FIG. 20, an exemplified WH 1600 includes the vehicle power connector 1601, the network processor 1602, a base band processor 1611, an RF transceiver 1612, an RF front end 1613, and an antenna array (or antenna arrays) 1514 (discussed in detail in connection with FIGS. 15B-15J above) in the long-range transmission circuit 1603 (FIG. 19). Antenna array(s) 1514 can be arranged as shown in FIGS. 15B and 15D or as arranged in FIG. 15E and 15F and connected to a switch 1522. In an alternative embodiment as shown in FIG. 15G, the antenna array could be a multi-layer antenna array 1530 receiving signals 1530 through power amplifiers 1532. Antenna arrays 1514 can be used for transmitting and receiving RF signals from selected directions. In another alternative embodiment as shown in FIG. 15H, the antenna array could be a multi-layer antenna array 1530 made up of EEA arrays 1514 which is part of an antenna array module 1533 that can be used to transmit or to receive RF signals (e.g., mmWave or microwave signals). The module 1533 includes circuitry necessary for RF communications such as power amplifiers 1532, phase shifters 1534, gain controllers 1536, splitters 1538, and low noise amplifiers 1540.

FIG. 15I shows that a multilayer EEA array 1530 could be made up of N+1 array 1514 layers in a range of 2 to 10 or greater with each layer 1514 capable of functioning independently or jointly. In another alternative embodiment as shown in FIG. 15J, the antenna array may be a multilayer EEA array 1530 that could be configured so that each layer 1514 can function independently or jointly (e.g., at different frequencies). Each layer can be used to transmit, to receive, or both to transmit and to receive for preferred directions at different frequencies. Each layer 1514 could be combined to shape the electromagnetic beam 1502.

The vehicle power connector 1601 can be plugged into a power socket 1202A built in the vehicle, which allows the WH 1600 to draw power from the car battery 1202B. In one implementation, the vehicle power connector 1601 is plugged into the car's cigarette lighter receptacle. In general, cigarette lighter receptacles can provide 12 volt and up to 10 amperes, which is much more than the battery power in existing personal hotspot devices. In another implementation, the vehicle power connector 1601 can also draw power from an I/O port (1651, FIG. 20), such as USB connectors and IPod chargers, which are increasingly popular in modern cars. If a car does not provide power to cigarette lighters or an I/O port while the car is off, a physical or software bypass can be implemented on the accessory switch of the car.

A vehicle's battery 1202B is much larger and has higher voltages than batteries in personal hotspot devices. An advantageous feature of the presently disclosed system is that the strong battery power in the vehicle 1202 allows the WH 1600 to extend its operational range beyond its associated vehicle 1202 to electronic devices such as mobile phone 1304 or 1710 (FIGS. 16-18B). For example, a vehicle based WH 1600 can provide short-range networks that operate farther than 0.25 mile, 0.5 mile, or one mile, which is a much wider range than short range wireless networks in existing personal hotspot technologies. Moreover, a vehicle based WH 1600 can also run for a longer operational period, without recharging the car battery, than personal hotspot devices. Because car batteries charge while the car is in motion, a vehicle based WH 1600 can operate indefinitely. The increased operational range and time allow the WH 1600 to become a more effective personal hub than conventional technologies. A power management unit 1652 can generate the appropriate voltage and current from the car battery 1202B.

The one or more short-range wireless transmission circuits 1604 (FIG. 19) in the WH 1600 each comprising a base band processor 1621, an RF transceiver 1622, and an RF front end 1623, and antenna 1624. Each RF front end can include power amplifiers, low noise amplifiers, switches, and filters, etc. Different short-range wireless transmission circuits 1604 can provide short-range wireless networks 1610 in different short-range wireless standards such as WiFi, Bluetooth™, and Zigbee. An antenna switch 1625 controls incoming and outgoing data flow among the different short-range wireless transmission circuits 1604. In some implementations, an antenna jack 1645 can be included, to connect to an auxiliary antenna to increase the operational range.

The network processor 1602 directs all incoming and outgoing data through the long-range wireless network 1640 and the short-range wireless networks 1610. The exemplified WH 1600 can also include an applications processor 1653, and a status indicator 1654 which can show the functional status and the operation mode (e.g. normal operation, reboot, no long-range connection, low power). The exemplified WH 1600 can also include an interface control 1655 to turn the WH 1600 on and or to change its range. The interface can use environmental sensors 1656 to sense the driver's or a passenger's gestures (e.g. hand waving movements) or voice instructions to control a vehicle . The exemplified WH 1600 can include an I/O port 1651 such as USB connectors, which can serve to either power other devices or act as a physical interface. Local data storage 1657 can be included to store data to enable the WH 1600 to act as a personal server. In this implementation, either the network processor 1602 or the application processor 1653 can handle the data flow, and control the writing and retrieval of data in the data storage 1657.

The WH 1600 can also include a global positioning system (GPS) 1658, accelerometers 1659, and environmental sensors (e.g., sound or video sensors) 1656 in communication with the network processor 1602. The GPS 1658 can make it easier for different vehicles 1202 to locate each other so that the WHs 1600 can generate the above described mesh networks between multiple vehicles. The accelerometers 1659 and environmental sensors 1656 allow users to monitor their vehicles with their electronic devices 1710 (FIGS. 16-18B). For example, environmental sensors can measure the temperature in the car to allow the user to remotely turn on the heater or air conditioning before the user enters the car. The sensors can also assure the safety and security of the vehicle.

In addition to the wireless standards discussed above, in alternative embodiments, it should be understood that the disclosed wireless systems are suitable for various standards and protocols for short-range and long-range wireless communications, such as Global System for Mobile communications (GSM), Universal Mobile Telecommunications Service (UMTS) Code Division Multiple Access (CDMA). GSM can include GPRS, EDGE and CSD. UMTS can include Wideband Code Division Multiple Access (WCDMA), High-Speed Packet Access (HSPA), High-Speed Downlink Packet Access (HSDPA), UMTS-TDD, Long Term Evolution (LTE), and LTE-Advanced. CDMA can include CDMA2000, and Ultra Mobile Broadband (UMB). Suitable wireless communications standards also include 3GPP, IMT-2000, WiMax, WiBro, WiFi, WLAN, 802.16, and others. Different wireless standards also include different software algorithms for signal encoding and decoding.

Figure 21A:
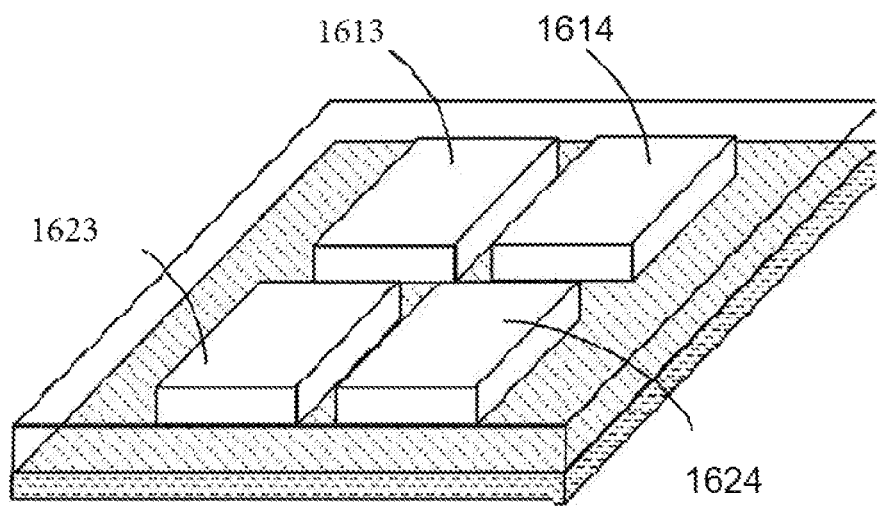
FIG. 21A shows the wireless hub 1600 in a package with integrated antennas.
Figure 21B:
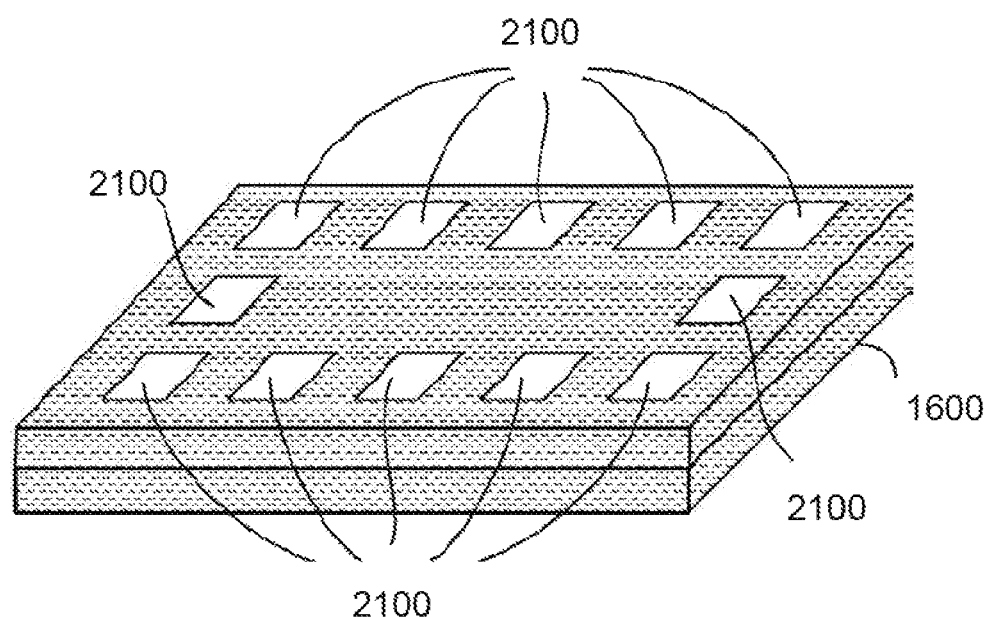
FIG. 21B shows the wireless hub 1600 in a package with an integrated antenna array.

FIG. 21A discloses another embodiment made of the WH 1600 discussed in connection with FIGS. 16-20 in a package arrangement of the long range wireless transmission circuit 1603 and short range transmission circuit 1604 and their associated antennas and antenna arrays. The package of FIG. 21A may be made up of all or some of the elements of FIGS. 16-20 including RF Front End 1613 and corresponding integrated antenna array (or arrays) 1514,1530 or 1533 for the long distance circuit, RF Front End 1623 and corresponding integrated antenna 1624 for the short distance circuit, antenna switch 1625 and antenna port 1645. RF transceivers 1612 and 1622, base band processors 1611 and 1621, network processor 1602, power management unit 1652, vehicle power connector 1601, applications processor 1653, sensors 1656, accelerometer 1659, GPS 1658, storage 1657, status indicator 1654, interface control 1655, and/or I/O port 1651 may also be in the WH 1600 arranged as shown in FIG. 20. The long range transmission circuit 1603 of the WH 1600, and corresponding integrated antenna 1514, may operate in 5G, 4G and/or the 3rd Generation Partnership Project Releases 15, 16, 17 and 18 for Fifth Generation ("5G") standards. As discussed above, the long range transmission circuit 1603, and corresponding integrated antenna arrays 1514, 1530 and/or 1533, is also capable of operating in millimeter wave frequencies (mm-Wave) (e.g., 10 GHz to 80 GHz) and microwave frequencies (e.g., 400 MHz to 7 GHz) while the short range transmission circuit 1604, and corresponding integrated antenna 1624, may operate in WiFi, Bluetooth, and Zigbee. FIG. 21B shows an alternative embodiment of FIG. 21A with integrated antenna elements 2100 arranged in an array which are connected to the long range wireless transmission circuit 1602. The antenna elements 2100 may be on the bottom side of the package of the WH 1600. The antenna elements 200 may also be on the side or the top of the package for best reception and transmission.

The WH 1600 shown in FIGS. 21A-21B may be made of Gallenium Arsenide (GaAs), Complementary Metal Oxide Semiconductor (CMOS), Silicon Germanium (SiGe), and Silicon on Insulator (SOI) and may include a splitter, phase shifter, gain controller, and input output (I/O).

Figure 22:
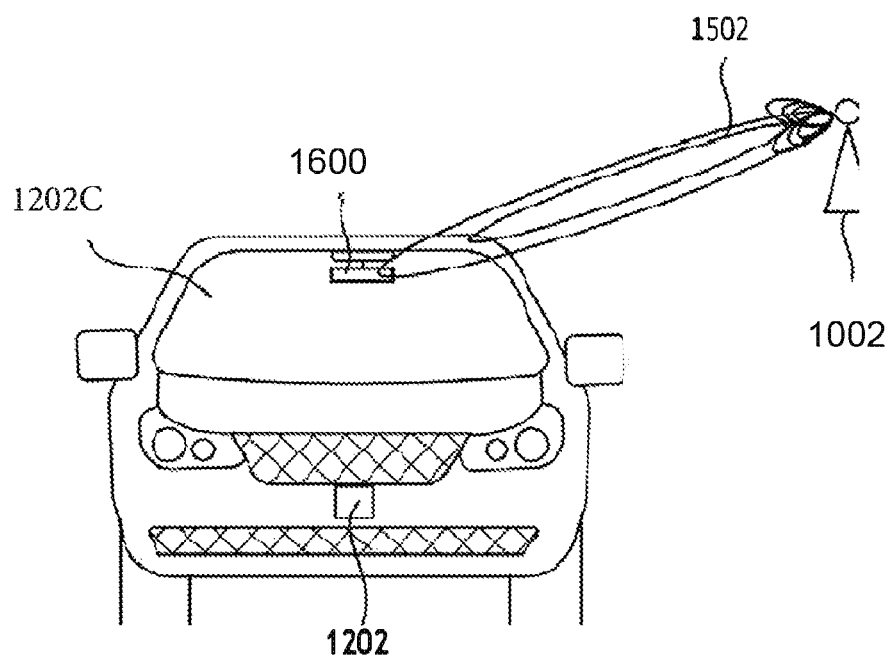
FIG. 22 shows an antenna embedded in and/or located on the outside of a vehicle.

FIG. 22 shows a base station 1002 (e.g., small cell, distributed antenna system, Pico cell, and/or Femto cell) transmitting signals 1003 to a vehicle 1202 and a WH 1600. Signals 1003 may be 5G, microwave and millimeter wave (mmWave). When the signal 1003 is transmitted to vehicle 1202 then all or a significant portion of the signal 1003 may be reflected off window 1202C and scattered. The WH 1600 may be attached (or mounted either outside the vehicle 1202 or any place inside the vehicle 1202). In some embodiments, the WH 1600 may be optimally placed on the surface of the vehicle 1202. The antenna arrays 1514, 1530 and/or 1533 may also be embedded in the frame or window 1202C and sealed off from the weather elements. Alternatively, the WH 1600 may be printed on a thin film material built either onto or embedded within window 1202C. WH 1600 can also be baked into vehicle window 1202C at low cost. The WH 1600 makes beam forming and steering of signal 1003 possible from the base station 1002.

In this disclosure, devices that are described as in "communication" with each other or "coupled" to each other need not be in continuous communication with each other or in direct physical contact, unless expressly specified otherwise. On the contrary, such devices need only transmit to each other as necessary or desirable, and may actually refrain from exchanging data most of the time. For example, a machine in communication with or coupled with another machine via the Internet may not transmit data to the other machine for long period of time (e.g. weeks at a time). In addition, devices that are in communication with or coupled with each other may communicate directly or indirectly through one or more intermediaries.

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Moreover, the illustration of a process by its depiction in a drawing does not imply that the illustrated process is exclusive of other variations and modifications thereto, does not imply that the illustrated process or any of its steps are necessary to the embodiment(s), and does not imply that the illustrated process is preferred.

It should be noted that the recitation of ranges of values in this disclosure are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, 1.9). The word "about" when accompanying a numerical value is to be construed as indicating a deviation of up to and inclusive of plus or minus 5% from the stated numerical value (e.g., frequency of approximately 40 GHz shall mean in a frequency range of 20 GHz to 60 GHz and inclusive of fractions between 20 GHz to 60 GHz).

Approximately: refers herein to a value that is almost correct or exact. For example, "approximately" may refer to a value that is within 1 to 10 percent of the exact (or desired) value. It should be noted, however, that the actual threshold value (or tolerance) may be application dependent. For example, in some embodiments, "approximately" may mean within 0.1% of some specified or desired value, while in various other embodiments, the threshold may be, for example, 2%, 3%, 5%, and so forth, as desired or as required by the particular application.

Automatically: refers herein to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Configured To: various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits. Various components may be described as performing a task or tasks, for convenience in the description. Such descriptions should be interpreted as including the phrase "configured to." Reciting a component that is configured to perform one or more tasks is expressly intended not to invoke 35 U.S.C. § 112(f) interpretation for that component.

Means Plus Function Language: to aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

The foregoing description and embodiments have been presented for purposes of illustration and description and are not intended to be exhaustive or to limit the embodiments in any sense to the precise form disclosed. Also, many modifications and variations are possible in light of the above teaching. The embodiments were chosen and described to best explain the principles of the disclosure and its practical application to thereby enable others skilled in the art to best use the various embodiments disclosed herein and with various modifications suited to the particular use contemplated. The actual scope of the invention is to be defined by the claims.

The invention claimed is:

1. A wireless hub comprising:
   and configured to directly send or receive data in frequencies ranging from approximately 10 GigaHertz (GHz) to approximately 80 GHz;
   wherein the first antenna has a plurality of antenna flat panels each having antenna array elements which are capable of wirelessly sending and receiving millimeter wave signals to and from at least one base station and at least one wireless hub, wherein the plurality of antenna flat panels are arranged to provide coverage to improve 360 degree reception for transmission and reception of the millimeter wave signals; and
   a second wireless transmission circuit connected to a second integrated antenna and configured to provide a short-range wireless network capable of sending or receiving data to and from electronic devices in the short-range wireless network.

2. The wireless hub of claim 1 comprising:
   a network processor configured to process data in the first wireless transmission circuit and the second wireless transmission circuit, wherein a vehicle power connector is configured to supply power to the first wireless transmission circuit, the second wireless transmission circuit, and the network processor.

3. The wireless hub of claim 1, wherein the second wireless transmission circuit is configured to transfer data to and from electronic devices in the short-range wireless network in a plurality of different wireless standards.

4. The wireless hub of claim 1, wherein the second wireless transmission circuit is configured to communicate in the short-range wireless network in at least one of the wireless standards: WiFi, Bluetooth™, or Zigbee.

5. The wireless hub of claim 1, wherein the second wireless transmission circuit comprises a base band processor, an RF transceiver, and an RF front-end circuit.

6. The wireless hub of claim 1, wherein the first wireless transmission circuit comprises a base band processor, an RF transceiver, and an RF front-end circuit.

7. The wireless hub of claim 1, further comprising:
   a power management unit configured to modify the voltage or current received from a vehicle power connector to supply power to the first wireless transmission circuit, the second wireless transmission circuit, and the network processor.

8. The wireless hub of claim 1, further comprising at least one of a global positioning system (GPS), an accelerometer, and an environmental sensor, which are in communication with the network processor and allow the electronic devices to monitor the location, the acceleration, temperature, safety, or security of a vehicle.

9. The wireless hub of claim 1, further capable of being attached to a vehicle.

10. The wireless hub of claim 9, further comprising:
    an application processor in communication with the network processor, wherein the application processor is configured to control the writing and retrieval of data in a server.

11. The wireless hub of claim 2, wherein the network processor and the second transmission circuit are configured to provide the short-range wireless network to electronic devices in the vehicle.

12. The wireless hub of claim 2, wherein the network processor and the second transmission circuit are configured to provide the short-range wireless network to electronic devices outside a vehicle.

13. The wireless hub of claim 2, wherein the network processor and the second transmission circuit are configured to provide the short-range wireless network to electronic devices while in motion.

14. The wireless hub of claim 1, wherein the network processor and the second transmission circuit are configured to communicate with the second short-range wireless transmission circuit in another vehicle to form a network mesh.

15. A wireless hub package comprising:
and configured to directly send or receive data in frequencies ranging from approximately 10 GigaHertz (GHz) to approximately 80 GHz with a base station and a plurality of vehicle wireless hubs;
wherein the first antenna has a plurality of antenna flat panels each having antenna array elements which are capable of wirelessly sending and receiving millimeter wave signals to and from at least one base station and at least one wireless hub, wherein the plurality of antenna flat panels are arranged to provide coverage to improve 360 degree reception for transmission and reception of the millimeter wave signals; and
a second wireless transmission circuit connected to a second package integrated antenna and configured to provide a short-range wireless network capable of sending or receiving data to and from electronic devices in the short-range wireless network.

16. The wireless hub package of claim 15, wherein the plurality of wireless hubs are capable of communicating while a vehicle is in motion.

17. A wireless hub package, comprising:
and configured to directly send or receive data in frequencies ranging from approximately 400 MegaHertz (MHz) to approximately 7 GigaHertz with base stations in a long-range wireless network and with another wireless hub;
wherein the first antenna has a plurality of antenna flat panels each having antenna array elements which are capable of wirelessly sending and receiving millimeter wave signals to and from at least one base station and at least one wireless hub, wherein the plurality of antenna flat panels are arranged to provide coverage to improve 360 degree reception for transmission and reception of the millimeter wave signals; and
a second wireless transmission circuit connected to a second integrated antenna and configured to provide a short-range wireless network capable of sending or receiving data to and from electronic devices in the short-range wireless network.

18. The system of claim 17, wherein the surrounding coverage is 360 degrees.

19. The system of claim 17, wherein the plurality of antenna flat panels form a quadrilateral configuration.

20. The system of claim 17, wherein the plurality of antenna flat panels form a hexagonal configuration.

* * * * *